(12) United States Patent
Zhang et al.

(10) Patent No.: US 9,518,059 B2
(45) Date of Patent: Dec. 13, 2016

(54) INHIBITOR CRYSTALLINE FORM AND PREPARATION METHOD AND USE THEREOF

(71) Applicant: Hangzhou Pushai Pharmaceutical Technology Co., LTD., Hangzhou (CN)

(72) Inventors: Zhonghua Zhang, Hangzhou (CN); Xiaoxia Sheng, Hangzhou (CN); Xiaohong Sheng, Hangzhou (CN)

(73) Assignee: HANGZHOU PUSHAI PHARMACEUTICAL TECHNOLOGY, Hangzhou (CN)

( * ) Notice: Subject to any disclaimer, the term of this patent is extended or adjusted under 35 U.S.C. 154(b) by 0 days.

(21) Appl. No.: 14/956,743

(22) Filed: Dec. 2, 2015

(65) Prior Publication Data

US 2016/0145258 A1 May 26, 2016

Related U.S. Application Data

(63) Continuation of application No. PCT/CN2014/083539, filed on Aug. 1, 2014.

(30) Foreign Application Priority Data

Aug. 1, 2013 (CN) .......................... 2013 1 0331680

(51) Int. Cl.
| | | |
|---|---|---|
| *A01N 43/90* | (2006.01) | |
| *A61K 31/52* | (2006.01) | |
| *C07D 473/34* | (2006.01) | |
| *C07D 473/00* | (2006.01) | |

(52) U.S. Cl.
CPC .................................. *C07D 473/34* (2013.01)

(58) Field of Classification Search
None
See application file for complete search history.

(56) References Cited

U.S. PATENT DOCUMENTS

2013/0252976 A1\* 9/2013 Carra .................. C07D 473/34
514/263.21

FOREIGN PATENT DOCUMENTS

| WO | WO 2005/113556 A1 | 12/2005 |
| WO | WO 2013/134288 A1 | 9/2013 |

OTHER PUBLICATIONS

Morissette et al. (Advanced Drug Delivery Reviews, 2004, 56, 275-300).\*
English Translation of the International Search Report for International Application No. PCT/CN2014/083539, State Intellectual Property Office of the P.R. China, China, mailed on Nov. 19, 2014, 3 pages.

\* cited by examiner

*Primary Examiner* — Dennis Heyer
*Assistant Examiner* — Daniel M Podgorski
(74) *Attorney, Agent, or Firm* — Sterne, Kessler, Goldstein & Fox PLLC

(57) ABSTRACT

The present invention relates to new crystalline forms of the inhibitor, 5-fluoro-3-phenyl-2-[(S)-1-(9H-purin-6-ylamino)-propyl]-3H-quinazoline-4-one; the present invention also relates to methods for preparing the new crystalline forms of 5-fluoro-3-phenyl-2-[(S)-1-(9H-purin-6-ylamino)-propyl]-3H-quinazolin-4-one, pharmaceutical compositions containing the new crystalline forms thereof, and uses thereof for the treatment and/or prevention of diseases such as chronic lymphocytic leukemia and indolent non-Hodgkin's lymphoma.

28 Claims, 19 Drawing Sheets

INHIBITOR CRYSTALLINE FORM AND PREPARATION METHOD AND USE THEREOF

FIELD OF THE INVENTION

The invention relates to the technical field of crystallization in pharmaceutical chemistry. Specifically, the present invention relates to novel crystalline polymorphic forms of PI3Kδ inhibitor 5-fluoro-3-phenyl-2-[(S)-1-(9H-purin-6-ylamino)-propyl]-3H-quinazoline-4-one (idelalisib) and processes for preparing such crystalline forms and method of their use, and pharmaceutical compositions comprising said novel crystalline forms.

BACKGROUND

Idelalisib is a phosphatidylinositol 3-kinase δ inhibitor (PI3Kδ inhibitor) developed by Gilead Sciences (USA) for treatment of chronic lymphocytic leukemia, indolent non-Hodgkin's lymphoma, mantle cell lymphoma, diffuse large B cell lymphoma, Hodgkin's lymphoma, multiple myeloma, acute myeloid leukemia and other hematological malignancies. The oral capsules are available in three strengths (100 mg, 150 mg and 300 mg). Idelalisib entered into a phase-III clinical study for treatment of chronic lymphocytic leukemia in 2012.

The chemical name of idelalisib is 5-fluoro-3-phenyl-2-[(S)-1-(9H-purin-6-ylamino)-propyl]-3H-quinazoline-4-one. Its English name is idelalisib or idelilisib. It is also known as GS-1101 or CAL-101. The chemical structural formula is shown below:

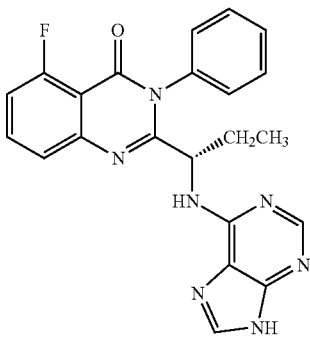 [SMILES: CC[C@H](Nc1ncnc2[nH]cnc12)c1nc2cccc(F)c2c(=O)n1-c1ccccc1]

Idelalisib

Example 9 in patent document WO2005113556A1 discloses idelalisib and a preparation process thereof. The disclosure of this patent document is hereby incorporated by reference in its entirety. Through repeated experiments, the inventors of the present invention discovered that the substance obtained according to the preparation process provided in WO2005113556A1 is a solvate of idelalisib with 0.4 molecule of ethanol (referred to as Form I in the present invention). However, the document did not provide characterization data of Form I. The inventors of the present invention discovered that Form I has the following defects: the weight change within the relative humidity range of 20~80% is about 0.95%, indicating that the crystalline form has some hygroscopicity; Form I is not very stable.

Therefore, there remains a practical significance to develop novel crystalline polymorphic forms of idelalisib with more advantageous properties.

SUMMARY OF THE INVENTION

The object of the present invention is to provide novel crystalline polymorphic forms of 5-fluoro-3-phenyl-2-[(S)-1-(9H-purin-6-ylamino)-propyl]-3H-quinazoline-4 one and processes for preparing such crystalline forms, methods of their use, and pharmaceutical compositions comprising said novel crystalline forms of idelalisib. Compared to Form I, novel crystalline forms disclosed by the present invention have one or more improved properties, particularly in good purity, improved thermodynamic stability, improved hygroscopicity under high humidity, and better formulation ability. The structural formula of is shown below.

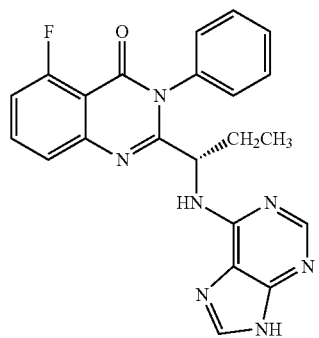 [SMILES: CC[C@H](Nc1ncnc2[nH]cnc12)c1nc2cccc(F)c2c(=O)n1-c1ccccc1]

Idelalisib

In the first aspect, the present invention provides a crystalline form II of idelalisib (referred to as Form II in the present invention) and preparation method thereof. Form II is an anhydrate.

Measured using Cu-Kα radiation, the X-ray powder diffraction pattern of Form II, expressed as 2θ angles, has the following characteristic peaks: 12.1±0.2°, 14.5±0.2°, 17.3±0.2°, 17.9±0.2°, 21.3±0.2° and 24.1±0.2°.

Preferably, the X-ray powder diffraction pattern of Form II, expressed as 2θ angles, has the following characteristic peaks: 12.1±0.2°, 14.5±0.2°, 16.5±0.2°, 17.3±0.2°, 17.9±0.2°, 21.3±0.2°, 23.8±0.2°, 24.1±0.2°, 24.8±0.2°, 25.2±0.2° and 29.4±0.2°.

Furthermore, the X-ray powder diffraction pattern of Form II, expressed as 2θ angles, has the following characteristic peaks with the following relative intensities:

| 2θ | Relative intensity % |
|---|---|
| 12.1 ± 0.2° | 52.8 |
| 14.5 ± 0.2° | 17.6 |
| 16.5 ± 0.2° | 14.1 |
| 17.3 ± 0.2° | 92.0 |
| 17.9 ± 0.2° | 100.0 |
| 21.3 ± 0.2° | 14.0 |
| 23.8 ± 0.2° | 7.9 |
| 24.1 ± 0.2° | 19.8 |
| 24.8 ± 0.2° | 8.5 |
| 25.2 ± 0.2° | 13.6 |
| 29.4 ± 0.2° | 6.2 |

Non-restrictively, in one specific embodiment of the present invention, the X-ray powder diffraction pattern of Form II is shown in FIG. 5.

The Fourier transform infrared spectroscopy (FTIR) spectrum of Form II has characteristic peaks at wavenumbers of 1688, 1613, 1590, 1568, 1473, 1453, 1386, 1328, 1300, 1252, 1231, 1160, 1097, 1036, 914, 820, 780, 765, 696, 668 and 617 $cm^{-1}$.

A preparation process of Form II comprises the following procedures: suspend Form I of idelalisib in a solvent system to form a suspension, stir the suspension at a crystallization temperature for crystallization, and then isolate and dry the precipitated solids to get Form II;

wherein, the solvent system is selected from the group consisting of toluene, a mixture of tetrahydrofuran and water, a mixture of ethanol and $C_3$-$C_4$ ketone, a mixture of ethanol and nitromethane, and a mixture of ethanol, $C_3$-$C_4$ ketone and nitromethane; preferably, the $C_3$-$C_4$ ketone is acetone or butanone.

In the mixture of tetrahydrofuran and water, the volume ratio of tetrahydrofuran to water is 2:1-1:2.

In the mixture of ethanol and $C_3$-$C_4$ ketone, the volume ratio of ethanol to $C_3$-$C_4$ ketone is 2:1-1:2.

In the mixture of ethanol and nitromethane, the volume ratio of ethanol to nitro methane is 2:1-1:2.

In the mixture of ethanol, $C_3$-$C_4$ ketone and nitromethane, the ratio of the total volume of $C_3$-$C_4$ ketone and nitromethane to the volume of ethanol is 2:1-1:2; and the volume ratio of $C_3$-$C_4$ ketone to nitromethane is in any proportion.

Preferably, the amount of Form I is 1.5-20 times of its solubility in corresponding solvent system at crystallization temperature; more preferably 1.5-10 times; and most preferably 2-5 times.

Preferably, the crystallization temperature is 0-40° C., and the duration of crystallization is 1-14 days; more preferably, the crystallization temperature is room temperature, and the duration of crystallization is 3-8 days.

Another preparation process of Form II comprises the following procedures: heat Form I, Form IV, Form V, Form VI, Form VII, Form VIII, Form IX or Form X of idelalisib, respectively, to 200-210° C. at a rate of 1-15° C./min, keep isothermal for 1-5 min until complete form transformation, and then cool naturally to get Form II.

Preferably, the heating rate is 10° C./min; the isothermal temperature is 200° C.; the duration of isothermal is 2 min; and cool to room temperature.

The complete form transformation may be verified by XRPD method to confirm complete transformation to Form II.

Form II has the following advantages:
① The weight change of Form II within the relative humidity range of 20-80% is only about 0.46%; compared to Form I (its weight change within the relative humidity range of 20-80% is about 0.95%), Form II is less hygroscopic.
② Form II is an anhydrate. Form I is a solvate with 0.4 molecule of ethanol. Compared to a solvate, an anhydrate has a higher active ingredient content.
③ When placed at room temperature (30-70% RH) for 3 months, Form II remained unchanged. It has good form stability.

In the second aspect, the present invention provides crystalline form III of idelalisib (referred to as Form III in the present invention) and preparation processes thereof. Form III is an anhydrate.

Measured using Cu-Kα radiation, the X-ray powder diffraction pattern of Form III, expressed as 2θ angles, has the following characteristic peaks: 12.3±0.2°, 17.8±0.2°, 14.2±0.2°, 15.9±0.2°, 18.1∓0.2° and 18.8±0.2°.

Preferably, the X-ray powder diffraction pattern of Form III, expressed as 2θ angles, has the following characteristic peaks: 12.3±0.2°, 12.8±0.2°, 14.2±0.2°, 15.9±0.2°, 16.3±0.2°, 17.4±0.2°, 17.9±0.2°, 18.1±0.2°, 18.8±0.2°, 19.6±0.2°, 20.6±0.2° and 24.5±0.2°.

Furthermore, the X-ray powder diffraction pattern of Form ill, expressed as 2θ angles, has the following characteristic peaks with the following relative intensities:

| 2θ | Relative intensity % |
|---|---|
| 11.9 ± 0.2° | 11.1 |
| 12.3 ± 0.2° | 59.3 |
| 12.8 ± 0.2° | 16.6 |
| 14.2 ± 0.2° | 16.9 |
| 15.9 ± 0.2° | 18.2 |
| 16.3 ± 0.2° | 14.3 |
| 17.4 ± 0.2° | 18.4 |
| 17.9 ± 0.2° | 18.1 |
| 18.1 ± 0.2° | 27.0 |
| 18.8 ± 0.2° | 100.0 |
| 19.6 ± 0.2° | 10.6 |
| 20.6 ± 0.2° | 13.5 |
| 21.4 ± 0.2° | 11.2 |
| 24.2 ± 0.2° | 14.8 |
| 24.5 ± 0.2° | 19.1 |

Non-restrictively, in one specific embodiment of the present invention, the X-ray powder diffraction pattern of Form III is shown in FIG. 9.

The FTIR spectrum of Form III has characteristic peaks at wavenumbers of 1689, 1623, 1589, 1569, 1473, 1454, 1384, 1328, 1300, 1251, 1231, 1159, 1098, 1067, 1036, 914, 820, 780, 766, 727, 696, 668 and 61.8 $cm^{-1}$.

A preparation process of Form III comprises the following procedures: suspend Form I of idelalisib in a solvent system to form a suspension, stir the suspension at a crystallization temperature for crystallization, and then isolate and dry the precipitated solids to get Form III. The solvent system is selected from the group consisting of acetonitrile, nitromethane and a mixed solvent of water and acetone with a volume ratio of water to acetone 2:1-1:2.

Preferably, the amount of Form I is 1.5-20 times of its solubility in the corresponding solvent system at the crystallization temperature; more preferably 1.5-10 times; and most preferably 2-5 times.

Preferably, the crystallization temperature is 0-40° C., and the duration of crystallization is 1-14 days; more preferably, the crystallization temperature is room temperature, and the duration of crystallization is 3-8 days.

Another preparation process of Form III comprises the following procedures: slurry one or more crystalline forms selected from the group consisting of Form I, Form II, Form IV and Form VIII of idelalisib in nitromethane for crystallization, and then isolate and dry the precipitated solids to get Form III.

Preferably, the amount of Form II, Form IV or Form VIII is 1.5-20 times of its solubility in nitromethane, more preferably 1.5-10 times and most preferably 2-5 times.

The slurry crystallization temperature is 10-40° C., and the duration of slurry crystallization is 3-110 days.

Form III has the following advantages:
① Placed at room temperature (30-70% RH) for 3 months, Form III remained unchanged. It has good form stability.
② The weight change of Form III within the relative humidity range of 20-80% is only about 0.44%; compared to Form I (its weight change within the relative humidity range of 20-80% is about 0.95%), Form III is less hygroscopic.
③ Form I and other novel crystalline forms of idelalisib disclosed by the present invention all transform to Form III in competitive slurry experiments, demonstrating Form III is thermodynamically the most stable form.

④ Form III is an anhydrate. Form I is a solvate with 0.4 molecule of ethanol. Compared to a solvate, an anhydrate has a higher active ingredient content.

In the third aspect, the present invention provides crystalline form IV of idelalisib (referred to as Form. IV in the present invention) and a preparation process thereof. Form IV is an anhydrate.

Measured using Cu-Kα radiation, the X-ray powder diffraction pattern of Form IV, expressed as 2θ angles, has the following characteristic peaks: 7.8±0.2°, 9.2±0.2°, 14.1±0.2°, 15.7±0.2°, 17.7±0.2°, 18.9±0.2° and 20.7±0.2°.

Preferably, the X-ray powder diffraction pattern of Form IV, expressed as 2θ angles, has the following characteristic peaks: 7.8±0.2°, 9.2±0.2°, 11.5±0.2°, 13.6±0.2°, 14.1±0.2°, 15.7±0.2°, 17.7±0.2°, 18.9±0.2°, 20.2±0.2°, 20.7±0.2°, 21.2±0.2°, 22.2±0.2° and 23.8±0.2°.

Furthermore, the X-ray powder diffraction pattern of Form IV, expressed as 2θ angles, has the following characteristic peaks with the following relative intensities:

| 2θ | Relative intensity % |
| --- | --- |
| 7.8 ± 0.2° | 65.7 |
| 9.2 ± 0.2° | 100.0 |
| 11.5 ± 0.2° | 25.9 |
| 13.6 ± 0.2° | 39.2 |
| 14.1 ± 0.2° | 91.4 |
| 15.7 ± 0.2° | 97.9 |
| 17.2 ± 0.2° | 10.5 |
| 17.7 ± 0.2° | 83.5 |
| 18.4 ± 0.2° | 12.8 |
| 18.9 ± 0.2° | 57.3 |
| 20.2 ± 0.2° | 39.3 |
| 20.7 ± 0.2° | 61.5 |
| 21.2 ± 0.2° | 29.6 |
| 21.8 ± 0.2° | 12.3 |
| 22.2 ± 0.2° | 31.2 |
| 22.8 ± 0.2° | 29.4 |
| 23.1 ± 0.2° | 17.6 |
| 23.8 ± 0.2° | 31.6 |
| 25.3 ± 0.2° | 22.2 |
| 25.8 ± 0.2° | 24.1 |
| 26.5 ± 0.2° | 17.0 |
| 27.1 ± 0.2° | 13.8 |
| 27.5 ± 0.2° | 12.5 |
| 27.9 ± 0.2° | 18.1 |
| 29.0 ± 0.2° | 16.3 |
| 29.7 ± 0.2° | 10.7 |

Non-restrictively, in one specific embodiment of the present invention, the X-ray powder diffraction pattern of Form IV is shown in FIG. 13.

The FTIR spectrum of Form IV has characteristic peaks at wavenumbers of 1698, 1628, 1590, 1568, 1475, 1453, 1412, 1329, 1296, 1231, 1152, 1096, 1036, 1025, 937, 901, 818, 801, 779, 755, 721, 694 and 610 cm$^{-1}$.

A preparation process of Form. IV comprises the following procedures: heat Form IX of idelalisib at a rate of 1-15° C./min to 100-150° C., keep isothermal for 1-5 min until complete form transformation, and then cool naturally to get Form IV.

Preferably, the heating rate is 10° C./min; the isothermal temperature is 110° C.; the duration of isothermal is 2 min; and cool to room temperature.

The complete form transformation may be verified by XRPD method to confirm complete transformation to Form IV.

Form IV has the following advantages:

① The weight change of Form IV within the relative humidity range of 20-80% is only about 0.3%; compared to Form I (its weight change within the relative humidity range of 20-80% is about 0.95%), Form IV is less hygroscopic.

② Placed at room temperature (30-70% RH) for 3 months, Form IV remained unchanged. It has good form stability.

③ Form IV is an anhydrate. Form I is a solvate with 0.4 molecule of ethanol. Compared to a solvate, an anhydrate has a higher active ingredient content.

The above advantages indicate, compared to Form I of idelalisib in the prior art, Form IV of idelalisib disclosed by the present invention exhibits multiple advantageous characteristics and may possess better application properties. Form IV of idelalisib disclosed by the present invention has good stability and low hygroscopicity. It is less likely to have content uniformity and stability issues caused by temperature and humidity during pharmaceutical production and storage, thus reduce the risk of efficacy decrease and safety issue caused thereby and improve dosing accuracy.

In the fourth aspect, the present invention provides crystalline form V of idelalisib (referred to as Form V in the present invention) and a preparation process thereof. Form V is a tetrahydrofuran solvate, containing about 1 tetrahydrofuran molecule per idelalisib molecule.

Measured using Cu-Kα radiation, the X-ray powder diffraction pattern of Form V, expressed as 2θ angles, has the following characteristic peaks: 7.6±0.2°, 11.0±02°, 17.6±0.2°, 18.2±0.2°, 19.5±0.2° and 21.6±0.2°.

Preferably, the X-ray powder diffraction pattern of Form V, expressed as 2θ angles, has the following characteristic peaks: 7.6±0.2°, 9.9±0.2°, 11.0±0.2°, 12.1±0.2°, 15.8±0.2°, 17.6±0.2°, 18.2±0.2°, 18.8±0.2°, 19.5±0.2°, 20.6±0.2°, 21.6±0.2° and 26.5±0.2°.

Furthermore, the X-ray powder diffraction pattern of Form V is substantially as shown in FIG. 17.

A preparation process of Form V comprises the following procedures: suspend Form I of idelalisib in tetrahydrofuran to form a suspension, stir at a crystallization temperature for crystallization, and then isolate and dry the precipitated solids to get Form V.

Preferably, the amount of Form I is 1.5-20 times of its solubility in tetrahydrofuran at the crystallization temperature; more preferably 1.5-10 times; and most preferably 2-5 times.

Preferably, the crystallization temperature is 0-40° C., and the duration of crystallization is 1-14 days; more preferably, the crystallization temperature is room temperature, and the duration of crystallization is 3-8 days.

In the fifth aspect, the present invention provides crystalline form VI of idelalisib (referred to as Form VI in the present invention) and a preparation process thereof. Form VI is a tetrahydrate.

Measured using Cu-Kα radiation, the X-ray powder diffraction pattern of Form VI, expressed as 2θ angles, has the following characteristic peaks: 9.8±0.2°, 11.3±0.2°, 13.3±0.2°, 17.5±0.2°, 19.3±0.2° and 23.2±0.2°.

Preferably, the X-ray powder diffraction pattern of Form VI, expressed as 2θ angles, has the following characteristic peaks: 9.8±0.2°, 11.3±0.2°, 12.5±0.2°, 13.3±0.2°, 17.1±0.2°, 17.5±0.2°, 19.3±0.2°, 22.1±0.2°, 22.7±0.2°, 23.2±0.2°, 23.6±0.2° and 26.4±0.2°.

Furthermore, the X-ray powder diffraction pattern of Form VI, expressed as 2θ angles, has the following characteristic peaks with the following relative intensities:

| 2θ | Relative intensity % |
|---|---|
| 9.8 ± 0.2° | 100.0 |
| 11.3 ± 0.2° | 28.4 |
| 11.6 ± 0.2° | 13.7 |
| 12.5 ± 0.2° | 25.9 |
| 13.3 ± 0.2° | 47.7 |
| 16.4 ± 0.2° | 12.7 |
| 16.8 ± 0.2° | 14.8 |
| 17.1 ± 0.2° | 24.2 |
| 17.5 ± 0.2° | 35.9 |
| 18.4 ± 0.2° | 30.1 |
| 19.3 ± 0.2° | 46.4 |
| 22.1 ± 0.2° | 25.1 |
| 22.7 ± 0.2° | 23.3 |
| 23.2 ± 0.2° | 46.7 |
| 23.6 ± 0.2° | 30.5 |
| 24.3 ± 0.2° | 11.1 |
| 26.4 ± 0.2° | 24.0 |
| 26.8 ± 0.2° | 12.4 |
| 28.5 ± 0.2° | 14.3 |
| 29.0 ± 0.2° | 19.0 |

Non-restrictively, in one specific embodiment of the present invention, the X-ray powder diffraction pattern of Form VI is shown in FIG. 20.

The FTIR spectrum of Form VI has characteristic peaks at wavenumbers of 3191, 1697, 1632, 1590, 1565, 1475, 1457, 1420, 1394, 1299, 1232, 1185, 1166, 1120, 1039, 1027, 953, 900, 819, 802, 781, 712, 695, 647 and 610 cm$^{-1}$.

A preparation process of Form VI comprises the following procedures: suspend Form I of idelalisib in a solvent system to form a suspension, stir at a crystallization temperature for crystallization, and then isolate and dry the precipitated solids to get Form VI; the solvent system is a mixed solvent of water and isopropanol or a mixed solvent of water and n-propanol.

Preferably, the volume ratio of water to isopropanol in the mixed solvent of water and isopropanol is 0.5:1-50:1 and more preferably 0.5:1-5:1; the volume ratio of water to n-propanol in the mixed solvent of water and n-propanol is preferably 0.5:1-50:1 and more preferably 0.5:1-5:1.

Preferably, the amount of Form I is 1.5-20 times of its solubility in the corresponding solvent system at the crystallization temperature, more preferably 1.5-10 times and most preferably 2-5 times.

Preferably, the crystallization temperature is 0-40° C., and the duration of crystallization is 1-14 days; more preferably, the crystallization temperature is room temperature, and the duration of crystallization is 3-8 days.

Form VI has the following advantages:
① The weight change of Form VI within the relative humidity range of 20-80% is only about 0.57%; compared to Form I (its weight change within the relative humidity range of 20-80% is about 0.95%), Form VI is less hygroscopic.
② Placed at room temperature (30-70% RH) for 3 months, Form VI remained unchanged. It has good form stability.
③ Form I is a solvate with 0.4 molecule of ethanol. Form VI is free of ethanol and thus is very suitable for patients who are hypersensitive to ethanol.

In the sixth aspect, the present invention provides crystalline form VII of idelalisib (referred to as Form VII in the present invention) and a preparation process thereof. Form VII is a methyl tert-butyl ether solvate, containing about 0.5 methyl tert-butyl ether molecule per idelalisib molecule.

Measured using Cu-Kα radiation, the X-ray powder diffraction pattern of Form VII, expressed as 2θ angles, has the following characteristic peaks: 7.7±0.2°, 9.9±0.2°, 11.1±0.2°, 16.0±0.2°, 17.7±0.2° and 18.1±0.2°.

Preferably, the X-ray powder diffraction pattern of Form VI, expressed as 2θ angles, has the following characteristic peaks: 7.7±0.2°, 9.9±0.2°, 11.1±0.2°, 14.6±0.2°, 15.1±0.2°, 16.0±0.2°, 17.7±0.2°, 18.1±0.2°, 19.6±0.2°, 20.5±0.2°, 24.1±0.2° and 26.6±0.2°.

Furthermore, the X-ray powder diffraction pattern of Form VII is substantially as shown in FIG. 24.

A preparation process of Form VII comprises the following procedures: suspend Form I of idelalisib in methyl tert-butyl ether to form a suspension, stir at a crystallization temperature for crystallization, and then isolate and dry the precipitated solids to get Form VII.

Preferably, the amount of Form I is 1.5-20 times of its solubility in methyl tert-butyl ether at the crystallization temperature; more preferably 1.5-10 times; and most preferably 2-5 times.

Preferably, the crystallization temperature is 0-40° C., and the duration of crystallization is 1-14 days; more preferably, the crystallization temperature is room temperature, and the duration of crystallization is 3-8 days.

In the seventh aspect, the present invention provides crystalline form VIII of idelalisib (referred to as Form VIII in the present invention) and a preparation process thereof. Form VIII is an anhydrate.

Measured using Cu-Kα radiation, the X-ray powder diffraction pattern of Form VIII, expressed as 2θ angles, has the following characteristic peaks: 9.5±0.2°, 11.4±0.2°, 12.4±0.2°, 12.7±0.2°, 15.1±0.2° and 18.8±0.2°.

Preferably, the X-ray powder diffraction pattern of Form VIII, expressed as 2θ angles, has the following characteristic peaks: 9.5±0.2°, 9.9±0.2°, 11.4±0.2°, 12.4±0.2°, 12.7±0.2°, 15.1±0.2°, 16.1±0.2°, 16.8±0.2°, 18.1±0.2°, 18.8±0.2°, 20.6±0.2° and 21.8±0.2°.

Furthermore, the X-ray powder diffraction pattern of Form VIII, expressed as 2θ angles, has the following characteristic peaks with the following relative intensities:

| 2θ | Relative intensity % |
|---|---|
| 9.5 ± 0.2° | 100.0 |
| 9.9 ± 0.2° | 9.2 |
| 11.4 ± 0.2° | 51.6 |
| 12.4 ± 0.2° | 37.7 |
| 12.7 ± 0.2° | 44.7 |
| 15.1 ± 0.2° | 33.1 |
| 16.1 ± 0.2° | 10.2 |
| 16.8 ± 0.2° | 18.4 |
| 18.1 ± 0.2° | 17.7 |
| 18.8 ± 0.2° | 37.2 |
| 20.6 ± 0.2° | 27.6 |
| 21.8 ± 0.2° | 15.7 |
| 26.1 ± 0.2° | 11.8 |

Non-restrictively, in one specific embodiment of the present invention, the X-ray powder diffraction pattern of Form VIII is shown in FIG. 27.

The FTIR spectrum of Form VIII has characteristic peaks at wavenumbers of 1697, 1630, 1589, 1569, 1473, 1453, 1388, 1329, 1298, 1252, 1232, 1153, 1097, 1036, 1025, 914, 875, 820, 797, 782, 763, 696, 647 and 616 cm$^{-1}$.

A preparation process of Form VIII comprises the following procedures: heat Form X of idelalisib at a rate of 1-15° C./mm to 150-200° C., keep isothermal for 1-5 min until complete form transformation, and then cool naturally to get Form VIII.

Preferably, the heating rate is 10° C./min; the isothermal temperature is 175° C.; the duration of isothermal is 2 min; and cool to room temperature.

The complete form transformation may be verified by XRPD method to confirm complete transformation to Form VIII.

Form VIII has the following advantages:
① The weight change of Form VIII within the relative humidity range of 20-80% is only about 0.84%; compared to Form I (its weight change within the relative humidity range of 20-80% is about 0.95%), Form VIII is less hygroscopic.
② Placed at room temperature (30-70% RH) for 3 months, Form VIII remained unchanged. It has good form stability.
③ Form VIII is an anhydrate. Form I is a solvate with 0.4 molecule of ethanol. Compared to a solvate, an anhydrate has a higher active ingredient content.

The above advantages indicate, compared to Form I of idelalisib, Form VIII of idelalisib disclosed by the present invention exhibits multiple advantageous characteristics and may possess better application properties. Form VIII of idelalisib has good stability and low hygroscopicity. It is less likely to have content uniformity and stability issues caused by temperature and humidity during pharmaceutical production and storage, thus reduce the risk of efficacy decrease and safety issue caused thereby and improve dosing accuracy.

In the eighth aspect, the present invention provides crystalline form IX of idelalisib (referred to as Form IX in the present invention) and a preparation process thereof. Form IX is a hydrate with 0.7 water molecule.

Measured using Cu-Kα radiation, the X-ray powder diffraction pattern of Form IX, expressed as 2θ angles, has the following characteristic peaks: 8.8±0.2°, 11.0±0.2°, 13.9±0.2°, 14.9±0.2°, 162±0.2° and 20.6±0.2°.

Preferably, the X-ray powder diffraction pattern of Form IX, expressed as 2θ angles, has the following characteristic peaks: 8.8±0.2°, 11.0±0.2°, 12.1±0.2°, 13.9±0.2°, 14.9±0.2°, 15.4±0.2°, 16.2±0.2°, 17.1±0.2°, 17.5±0.2°, 20.6±0.2°, 23.2±0.2° and 24.1±0.2°.

Furthermore, the X-ray powder diffraction pattern of Form IX, expressed as 2θ angles, has the following characteristic peaks with the following relative intensities:

| 2θ | Relative intensity % |
|---|---|
| 8.8 ± 0.2° | 100.0 |
| 11.0 ± 0.2° | 88.1 |
| 12.1 ± 0.2° | 12.1 |
| 13.9 ± 0.2° | 79.4 |
| 14.9 ± 0.2° | 33.3 |
| 15.4 ± 0.2° | 19.9 |
| 16.2 ± 0.2° | 51.2 |
| 17.1 ± 0.2° | 17.3 |
| 17.5 ± 0.2° | 25.6 |
| 20.6 ± 0.2° | 44.7 |
| 20.9 ± 0.2° | 11.2 |
| 21.8 ± 0.2° | 11.6 |
| 23.2 ± 0.2° | 19.8 |
| 23.8 ± 0.2° | 16.0 |
| 24.1 ± 0.2° | 25.5 |
| 24.6 ± 0.2° | 22.5 |
| 27.8 ± 0.2° | 14.2 |

Non-restrictively, in one specific embodiment of the present invention, the X-ray powder diffraction pattern of Form. IX is shown in FIG. 31.

The FTIR spectrum of Form IX has characteristic peaks at wavenumbers of 1675, 1607, 1472, 1382, 1326, 1301, 1233, 1184, 1100, 1036, 946, 821, 798, 785, 718, 698 and 649 $cm^{-1}$.

A preparation process of Form IX comprises the following procedures: suspend Form I of idelalisib in a solvent system of water and ethanol to form a suspension, stir or sonicate at a crystallization temperature for crystallization, and then isolate and dry the precipitated solids to get Form IX.

The volume ratio of ethanol to water in the solvent system is 1:1-4:10, preferably 1:4-1:10.

Preferably, the amount of Form I is 1.5-20 times of its solubility in the corresponding solvent system at the crystallization temperature; more preferably 1.5-10 times; and most preferably 2-5 times.

Preferably, the stirring crystallization temperature is 0-40° C., and the duration of stirring crystallization is 1-14 days; more preferably, the stirring crystallization temperature is room temperature, and the duration of stirring crystallization is 3-8 days.

Preferably, the crystallization by sonication refers to sonicate at a working power of 20~40 Khz at room temperature for 1~3 hours.

Form IX has the following advantages:
① The weight change of Form IX within the relative humidity range of 20-80% is only about 0.3%; compared to Form I (its weight change within the relative humidity range of 20-80% is about 0.95%), Form IX is less hygroscopic.
② Placed at room temperature (30-70% RH) for 3 months, Form IX remained unchanged. It has good form stability.
③ Form I is a solvate with 0.4 molecule of ethanol. Form IX is free of ethanol and thus is very suitable for patients who are hypersensitive to ethanol.
④ Compared to Form I, Form IX is more stable in the ethanol-water system (volume ratio of ethanol to water is 1:1-1:10) and thus more suitable for wet granulation.

The above advantages indicate, compared to Form I of idelalisib, Form of idelalisib disclosed by the present invention exhibits multiple advantageous characteristics and may possess better application properties. Form. IX of idelalisib has good stability and low hygroscopicity. It is less likely to have content uniformity and stability issues caused by temperature and humidity during pharmaceutical production and storage, thus reduce the risk of efficacy decrease and safety issue caused thereby and improve dosing accuracy. In addition, for a solid formulation processed by wet granulation, Form IX has more advantages.

In the ninth aspect, the present invention provides crystalline form X of idelalisib (referred to as Form X in the present invention) and a preparation process thereof. Form X is a dioxane solvate, containing about 0.8 dioxane molecule per idelalisib molecule.

Measured using Cu-Kα radiation, the X-ray powder diffraction pattern of Form X, expressed as 2θ angles, has the following characteristic peaks: 7.9±0.2°, 11.1±0.2°, 15.6±0.2°, 17.4±0.2°, 18.4±0.2° and 19.5±0.2°.

Preferably, the X-ray powder diffraction pattern of Form X, expressed as 2θ angles, has the following characteristic peaks: 7.9±0.2°, 10.1±0.2°, 11.1±0.2°, 14.2±0.2°, 15.6±0.2°, 17.4±0.2°, 18.4±0.2°, 19.5±0.2°, 20.0±0.2°, 21.1±0.2°, 21.9±0.2° and 26.2±0.2°.

Furthermore, the X-ray powder diffraction spectrum of Form X is substantially as shown in FIG. 35.

A preparation process of Form X comprises the following procedures: suspend Form I of idelalisib in dioxane to form a suspension, stir at a crystallization temperature for crystallization, and then isolate and dry the precipitated solids to get Form X.

Preferably, the amount of Form I is preferably 1.5-20 times its solubility in dioxane at the crystallization temperature; more preferably 1.5-10 times; and most preferably 2-5 times.

Preferably, the crystallization temperature is 0-40° C., and the duration of crystallization is 1-14 days; more preferably, the crystallization temperature is room temperature, and the duration of crystallization is 3-8 days.

In the present invention, Form II, Form IV, Form VIII and Form I transform into Form III in a nitromethane slurry; Form IX transforms into Form VI in a isopropanol and water slurry.

In the preparation methods for Form II, Form III, Form IV, Form V, Form VI, Form VII, Form VIII, Form IX and Form X disclosed by the present invention:

Form I is the ethanol solvate of idelalisib with each molecule of ethanol solvate of idelalisib comprising 0.4 molecule of ethanol and may be prepared by the process disclosed in example 9 of WO2005113556A1.

The room temperature refers to 10-30° C.

The stirring or agitation may be performed by routine methods in the field. For example, stirring methods include magnetic stirring and mechanical stirring. The stirring speed is 50~1800 r/min, preferably 300~900 r/min.

The separation may be performed by routine methods in the field, such as filtration and centrifugation. The detailed operation of filtration is: place the sample to be separated on filter paper and vacuum filter it under reduced pressure. The detailed operation of centrifugation is: place the sample to be separated in a centrifuge tube, rotate at a high speed until the solid completely settles at the bottom of the tube. The centrifugation speed is, for example, 6000 r/min.

The drying may be performed by routine methods in the field, such as blast drying and drying under reduced pressure. The drying temperature is 30-120° C., preferably 40-80° C. and more preferably 40-60° C.; the drying time is 10-72 hours, preferably 10-48 hours and more preferably 10-24 hours. In vacuum drying, the pressure is preferably <0.09 MPa. Drying may be performed in a fume hood, a blast oven or a vacuum oven.

The detailed operation of the sonication is: place the container with the solution or suspension in an ultrasonic cleaner and sonicate at 20~40 Khz.

Unless particularly specified, the anhydrate in the present invention refers to a crystalline form containing no more than 1.5% (weight ratio) or no more than 1.0% (weight ratio) of water as measured by TGA.

The slurry preparation refers to stirring or agitating a supersaturated solution of the sample (with undissolved solids) in a solvent system.

The slurry method described in the present invention refers to stirring of a supersaturated solution of the sample (with undissolved solids) in various solvent systems for crystallization. Usually, the duration is 14 days.

Novel anhydrous crystalline forms of idelalisib including Form II, Form III, Form IV and Form VIII of the present invention are superior to Form I in the prior art in that: Form I is an ethanol solvate which ultimately has lower API content; and the novel anhydrous crystalline forms are less hygroscopic than Form I and are thermodynamically more stable under humidity. In addition, novel hydrates of idelalisib including Form VI and Form IX of the present invention have lower hygroscopicity and have better thermodynamic stability under humidity, which overcomes flaws of Form I in the prior art.

Furthermore, the present invention provides a pharmaceutical composition, which comprises a therapeutically and/or preventively effective amount of one or more novel crystalline forms provided by the present invention or novel crystalline forms prepared using processes provided by the present invention and at least one pharmaceutically acceptable excipient. The novel crystalline forms of idelalisib include Form II, Form III, Form IV, Form V, Form VI, Form VII, Form VIII, Form IX and Form X. Moreover, the pharmaceutical composition may also comprises other pharmaceutically acceptable crystalline forms (e.g. Form I) or the amorphous form or salt forms of idelalisib.

Administrative routes of the above pharmaceutical compositions include oral administration, intravenous injection and subcutaneous injection, injection into tissue, transdermal administration, rectal administration, nasal dripping, etc. The pharmaceutical compositions may be a solid or a liquid. Its dosage form may be a solid oral dosage form, including tablets, granules, pulvisie, pills or capsules; which may be regular tablets or capsules, dispersible tablets, chewable tablets, orally soluble tablets or rapidly dissolving tablets; an oral liquid dosage form, including solution, syrup, suspension, dispersion or emulsion; parental dosage forms, including solution, dispersion or lyophilized dosage forms. The formulation may be suitable for rapid release, delayed release or controlled release of the active ingredient. If the pharmaceutical composition is a liquid dosage form, Form II, Form III, Form IV, Form V, Form VI, Form VII, Form VIII, Form IX and Form X of idelalisib may remain in solid state, such as in suspension.

The pharmaceutical compositions may be prepared by a method commonly known to those skilled in the art. In preparation of the pharmaceutical compositions, novel crystalline forms of idelalisib disclosed by the present invention or combinations thereof are mixed with one or more pharmaceutically acceptable excipients, optionally with other pharmaceutically acceptable crystalline forms (e.g. Form I), amorphous forms or salt forms of idelalisib, optionally with one or more other active ingredients. Solid dosage forms may be prepared by direct mixing, granulation and other processes.

The pharmaceutically acceptable excipients in the present invention include but are not limited to: diluents, e.g. starch, pregelatinized starch, lactose, powdered cellulose, microcrystalline cellulose, calcium hydrogen phosphate, tricalcium phosphate, mannitol, sorbitol, and sugar, etc.; adhesives, e.g. Arabia gum, guar gum, gelatin, polyvinylpyrrolidone, hydroxypropyl cellulose, hydroxypropyl methylcellulose, and polyethylene glycol, etc.; disintegrants, e.g. starch, sodium starch glycolate, pregelatinized starch, cross-linked polyvinyl polypyrrolidone, cross-linked sodium carboxymethylcellulose, and colloidal silica dioxide, etc.; lubricants, e.g. stearic acid, magnesium stearate, zinc stearate, sodium benzoate, and sodium acetate, etc.; glidants, e.g. colloidal silica dioxide; complex forming agents, e.g. cyclodextrin and resins of various grades; release rate controllers, e.g. hydroxypropyl cellulose, carboxymethyl cellulose, hydroxypropyl methyl cellulose, ethyl cellulose, methyl cellulose, methyl methacrylate, and wax, etc. Other pharmaceutically acceptable excipients include but are not limited to film forming agents, plasticizers, coloring agents, flavoring agents, viscosity regulators, preservatives, and antioxidants, etc.

Furthermore, the present invention provides use of one or more novel crystalline forms of idelalisib provided by the present invention or novel crystalline forms of idelalisib prepared using the processes provided by the present invention in treating and/or preventing chronic lymphocytic leukemia, indolent non-Hodgkin's lymphoma, mantle cell lymphoma, diffuse large B cell lymphoma, Hodgkin's lymphoma, multiple myeloma, acute myeloid leukemia and other hematological malignancies. The novel crystalline forms of idelalisib include Form II, Form III, Form IV, Form V, Form VI, Form VII, Form VIII, Form IX and Form X.

Furthermore, the present invention provides a method for treating and/or preventing chronic lymphocytic leukemia, indolent non-Hodgkin's lymphoma, mantle cell lymphoma, diffuse large B cell lymphoma, Hodgkin's lymphoma, multiple myeloma, acute myeloid leukemia and other hematological malignancies. The method comprises administratering to a patient in need a therapeutically and/or preventatively effective amount of novel crystalline forms of idelalisib in the present invention or their combinations or pharmaceutical compositions containing these novel crystalline forms. The novel crystalline forms of idelalisib include Form II, Form III, Form IV, Form V, Form VI, Form VII, Form VIII, Form IX and Form X. The patients include but are not limited to mammals. The human dose is about 0.001~100 mg/kg. The unit dosage of the active ingredient usually depends on the administration route and indications, and is about 0.01~10000 mg, preferably about 0.1~1000 mg. Depending on the administration route, an appropriate dose may be calculated based on the body weight, the body surface area or organ sizes; by considering multiple factors in improving drug action, for example, specific activity of the active ingredient, the characteristics and severity of the disease, patient responses, age, physical conditions, body weight, gender, diet, etc., clinical physicians may establish a final dosing based on good medical practices.

EXAMPLES

Figure 1:
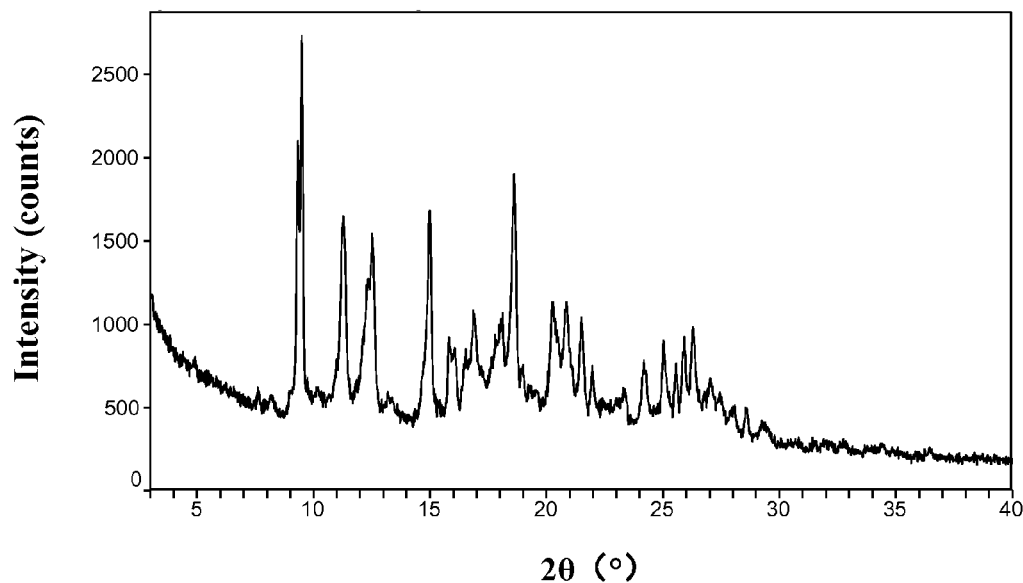
FIG. 1 is the XRPD pattern of Form I prepared by reference to WO2005113556A1.

The following examples are given for further understanding the present invention but are not used for limiting the disclosure of the present invention. It will be apparent to those skilled in the art from this disclosure that various modifications can be made to materials and methods without departing from the scope of the present invention.

Instruments and Methods Used for Data Collection:

X-ray powder diffraction (XRPD) was performed on a Balker D8 Advance Diffractometer configured with a θ-2θ goniometer, a Mo monochrometer and a Lynxeye detector. The collection software is Diffrac Plus XRPD Commander. Before using, the instrument was performance checked using the provided standard (usually corundum). The following testing conditions were used: 2θ scan range, 3-40°; step size, 0.02°; speed, 0.2 s/step. Testing procedure: using a Cu-Kα radiation with a wavelength of 1.54 nm, the sample was analyzed on an organic slide at room temperature at 40 kV and 40 mA. Unless particularly specified, samples had not been grinded prior to analysis.

Differential scanning calorimetry (DSC) data were collected using TA Instruments Q200 MDSC. The instrument control software was Thermal Advantage, and the analytical software was Universal Analysis. Usually, 1-10 mg of the sample was placed in an uncovered (unless particularly specified) aluminum pans and heated at a rate of 10° C./min from room temperature to 250° C. under the protection of dry $N_2$ at a flow rate of 50 mL/min while the TA software was recording heat changes of the sample during the heating process. In the present application, melting points are reported as melting ranges.

Thermogravimetric analysis (TGA) data were collected using TA Instruments Q500 TGA. The instrument control software was Thermal AdVantage, and the analytical software was Universal Analysis. Usually, 5-15 mg of the sample was placed in a platinum pan, by segmental high-resolution detection, the sample was heated at a rate of 10° C./min from room temperature to 300° C. under the protection of dry $N_2$ at a flow rate of 50 mL/min while the TA software was recording weight changes of the sample during the heating process.

Dynamic vapor sorption (DVS) data were collected using TA Instruments Q500 TGA. The instrument control software was Thermal Advantage, and the analytical software was Universal Analysis. Usually, 1-10 mg of the sample was placed in a platinum pan, and the weight change of the sample during studies was recorded. The relative humidity was usually programed to change from 50% to 80% to 0% and then back to 50%, and an isothermal sorption plot could be generated. Depending on specific situations, different sorption and desorption procedures might be used.

Infrared spectrometry (IR) data were collected using Bruker Tensor 27 equipped with an attenuated total reflection (ATR). OPUS was used both for instrument control and data analysis. Usually, the infrared spectra were collected over 600-4000 $cm^{-1}$. Both samples and the blank background were scanned for 16 s. The instrument resolution was 4 $cm^{-1}$.

High performance liquid chromatography (HPLC) data were collected using Agilent HPLC 1260 under the following conditions: column, VP-ODS 150×4.6H-019#; column temperature, 25° C.; flow rate, 1 mL/min, detection wavelength, 220 nm; injection volume, 5 μL; running time, 15 min; solvent, water: acetonitrile=1:1; preparation of sample solution: 5 mg sample, q.s. with the solvent to 10 μL. The following mobile phase was used:

| Time (min) | Water (%) | Acetonitrile (%) |
|---|---|---|
| 0 | 70 | 30 |
| 8 | 10 | 90 |
| 13 | 10 | 90 |
| 13.01 | 70 | 30 |
| 15 | 70 | 30 |

Example 1

Form I of idelalisib was prepared by reference to the process described in example 9 in WO2005113556A1. The operating procedures are detailed as follows: at 80° C., a suspension of (S)-2-(1-amino-propyl)-5-fluoro-3-phenyl-3H-quinazoline-4-one (65.6 mmol, 1 equivalent), 6-bromopurine (14.6 g, 73.4 mmol, 1.1 equivalents) and & isopropyl ethylamine (24.3 mL, 1.40 mmol, 2 equivalents) in tertiary butyl alcohol (40 mL) was stirred for 24 hours; the reaction mixture was concentrated under vacuum and processed with water to get the solid crude product, which was concentrated under vacuum, collected, washed with water and allowed to dry. Half of the obtained solid crude product was dissolved in 600 mL of methanol, concentrated onto silica gel (300 mL, dry), separated and purified by rapid chromatography (7.5×36 mm, eluted with 10 L of 4% methanol/dichloromethane) and concentrated to obtain a solid. The solid was dissolved in 250 mL of ethanol and concentrated under vacuum, producing a pale yellow solid compound. Elemental analysis showed that the product was ethanol solvate of idelalisib with 0.4 molecule of ethanol.

$^1$HNMR (300 MHz, DMSO-d6): d12.66 (broad s, 1H), 8.11 (s, 1H), 8.02 (broad s, 1H), 7.81-7.73 (m, 1H), 7.60-7.42 (m, 6H), 7.25-7.15 (m, 2H), 4.97 (broad s, 1H), 2.02-1.73 (m, 2H), 0.79 (t, J=7.3 Hz, 3H), indicating the product was idelalisib.

Figure 2:
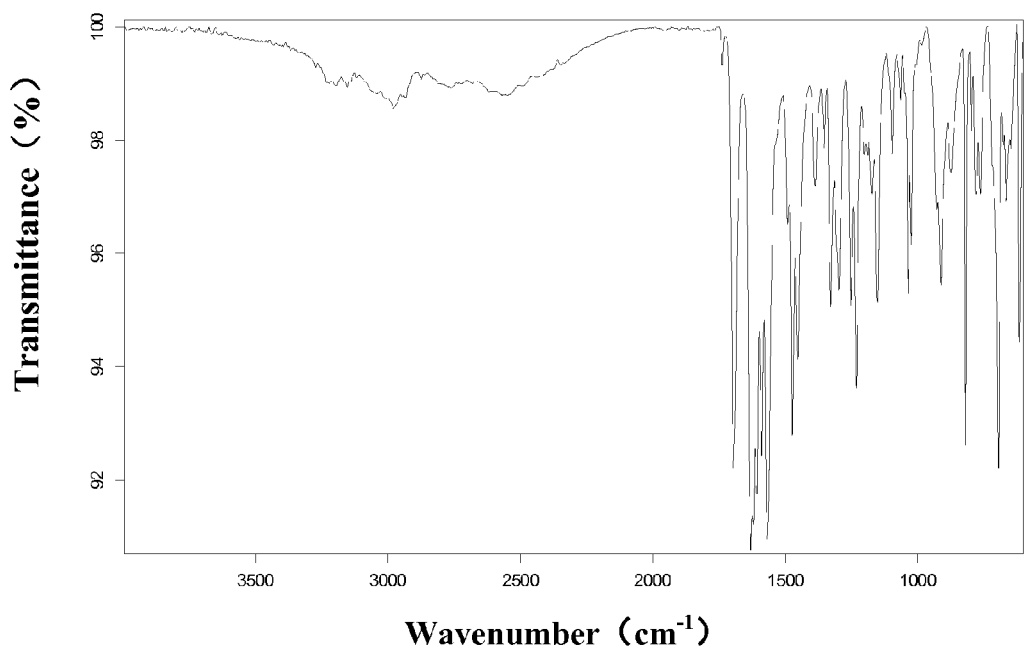
FIG. 2 is the IR spectrum of Form I prepared by reference to WO2005113556A1.
Figure 3:
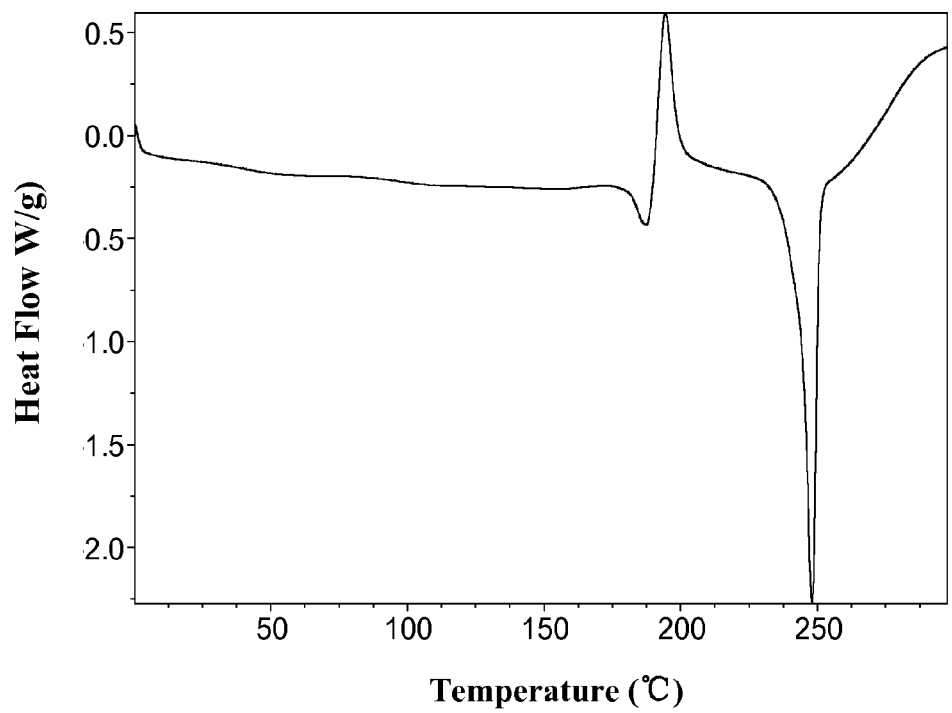
FIG. 3 is the DSC thermogram of Form I prepared by reference to WO2005113556A1.
Figure 4:
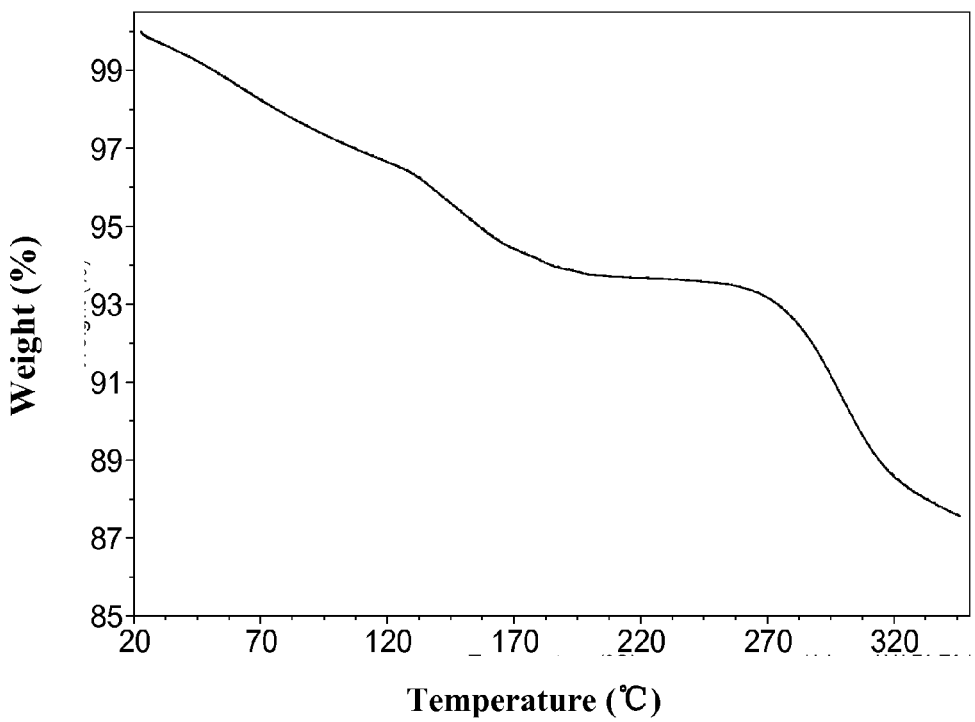
FIG. 4 is the TGA thermogram of Form I prepared by reference to WO2005113556A1.

The X-ray powder diffraction pattern is shown in FIG. 1.
The IR spectrum is shown in FIG. 2.
The DSC thermogram is shown in FIG. 3, indicating: the melting range of Form I was 181-188° C.; an exothermic form transformation peak was observed at 190-208° C.; the melting range of the sample after form transformation was 244-248° C.; Form II was formed after form transformation.
The TGA thermogram is shown in FIG. 4, indicating: a weight loss of about 4.7% occurred before 150° C. (1 idelalisib molecule is associated with about 0.4 molecule of ethanol); the decomposition temperature was 276° C.
DVS indicates: the weight change within the relative humidity range of 20%-80% was 0.95%.

Example 2

To 102.8 mg of Form I of idelalisib in a 10 mL glass vial, 5 mL of toluene was added. A suspension was obtained after sonication for 5 min. The suspension was stirred at room temperature for 8 days for crystallization. The obtained solid was filtered and dried under vacuum at 60° C. for 10 hours. Form II in the present invention was obtained. The product was 94.3 mg; the molar yield was 95.8%.

Figure 5:
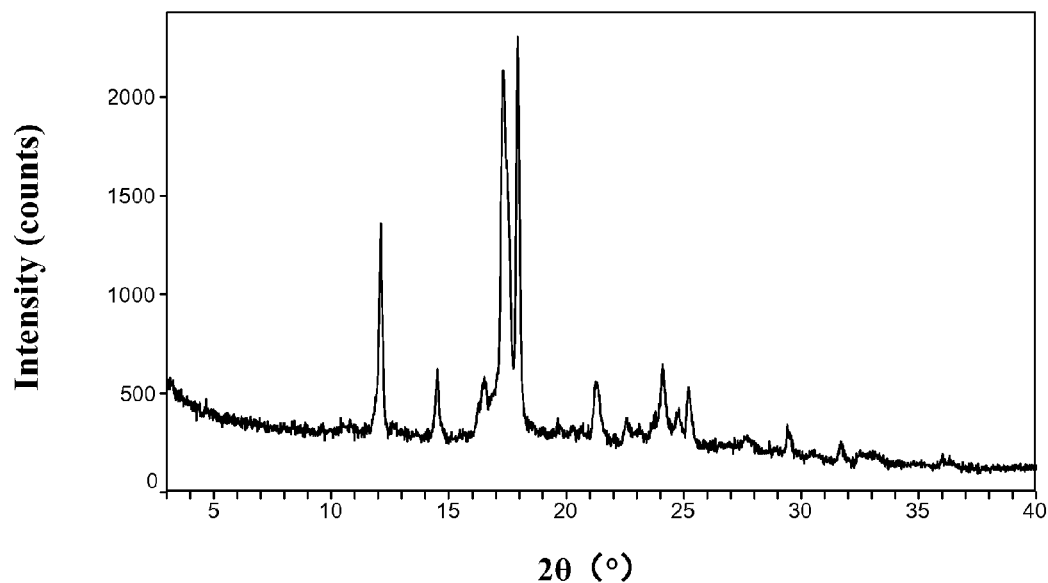
FIG. 5 is the XRPD pattern of Form II provided by the present invention.
Figure 6:
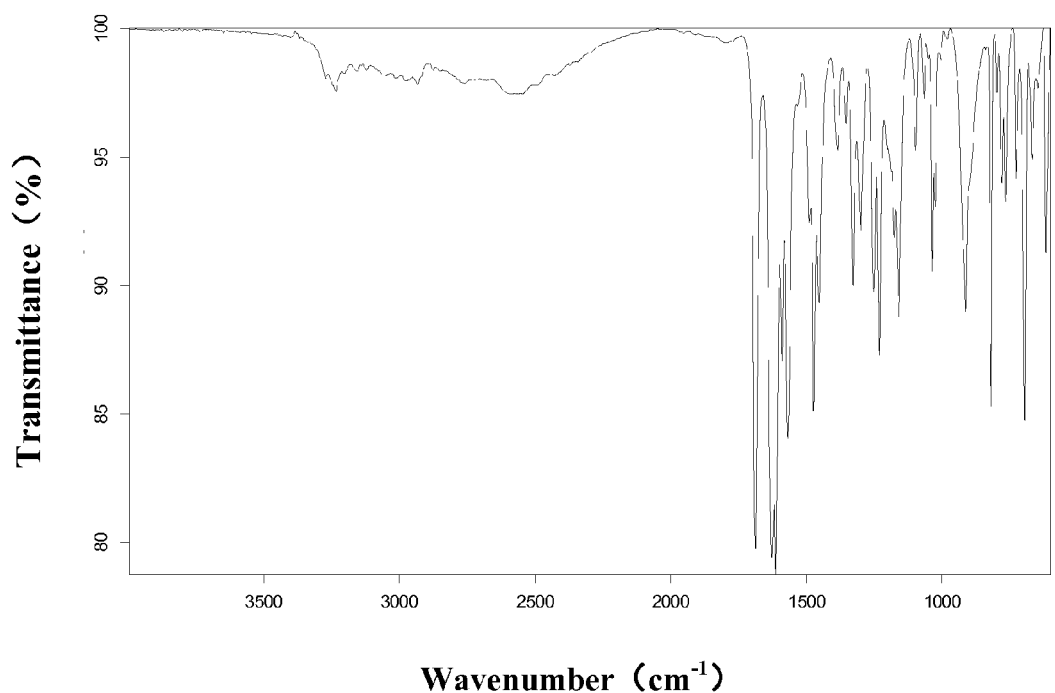
FIG. 6 is the IR spectrum of Form II provided by the present invention.
Figure 7:
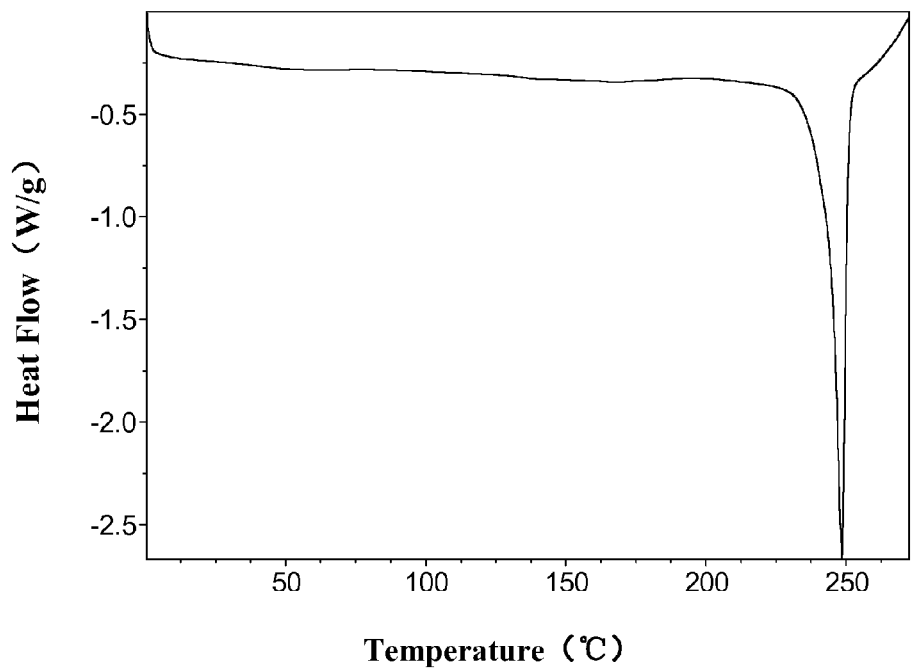
FIG. 7 is the DSC thermogram of Form II provided by the present invention.
Figure 8:
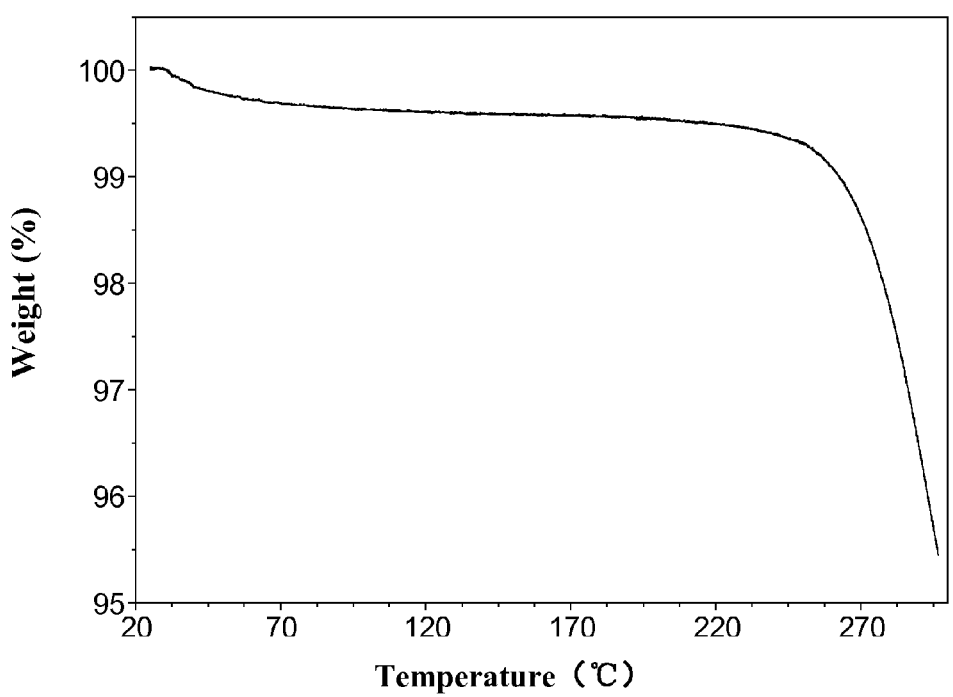
FIG. 8 is the TGA thermogram of Form II provided by the present invention.

The X-ray powder diffraction pattern is shown in FIG. 5.
The IR spectrum is shown in FIG. 6.
The DSC thermogram is shown in FIG. 7, indicating: the melting range was 244-249° C.
The TGA thermogram is shown in FIG. 8, indicating: a weight loss of about 0.41% occurred before 150° C. (anhydrate); the decomposition temperature was 271° C.
DVS indicates: the weight change within the relative humidity range of 20%-80% was 0.46%.

Example 3

To 102.8 mg of Form I of idelalisib in a 15 mL glass vial, 5 mL of water and 5 mL of tetrahydrofuran were added. A suspension was obtained after sonication for 5 min. The suspension was stirred at 40° C. for 1 day for crystallization. The obtained solid was filtered and dried under vacuum at 40° C. for 24 hours. Form II in the present invention was obtained. The product was 80.2 mg; the molar yield was 81.5%.

Example 4

To 85.28 mg of Form I of idelalisib in a 5 mL glass vial, 2 mL of ethanol and 2 mL of acetone were added. A suspension was obtained after sonication for 5 min. The suspension was stirred at 0° C. for 14 days for crystallization. The obtained solid was filtered and dried in a blasting oven at 120° C. for 24 hours. Form II in the present invention was obtained. The product was 59.0 mg; the molar yield was 72.3%.

Example 5

To 80.08 mg of Form I of idelalisib in a 5 mL glass vial, 2 mL of ethanol and 2 mL of butanone were added. A suspension was obtained after sonication for 5 min. The suspension was stirred at room temperature for 3 days for crystallization. The obtained solid was filtered and dried under vacuum at 30° C. for 72 hours. Form II in the present invention was obtained. The product was 60.9 mg; the molar yield was 79.4%.

Example 6

To 111.36 mg of Form I of idelalisib in a 10 mL glass vial, 3 mL of ethanol and 3 mL of nitromethane were added. A suspension was obtained after sonication for 5 min. The suspension was stirred at room temperature for 8 days for crystallization. The obtained solid was filtered and dried under vacuum at 60° C. for 10 hours. Form II in the present invention was obtained. The product was 91.3 mg; the molar yield was 85.6%.

Example 7

5.48 mg of Form I of idelalisib was studied by a DSC instrument following the procedures below: the sample was heated at a rate of 10° C./min to 200° C. and held for 2 min and then cooled naturally to room temperature. Form II in the present invention was obtained. The product was 5.25 mg; the yield was 100%.

The XRPD patterns, IR spectra, DSC thermograms and TGA thermograms obtained from samples prepared in examples 3-7 were the same or similar as those obtained from the sample prepared in example 2, indicating the crystalline form obtained in examples 3-7 was the same as that obtained in example 2.

Example 8

To 118.08 mg of Form I of idelalisib in a 10 mL glass vial, 6 mL of acetonitrile was added. A suspension was obtained after sonication for 5 min. The suspension was stirred at room temperature for 8 days for crystallization. The obtained solid was filtered and dried under vacuum at 60° C. for 10 hours. Form III in the present invention was obtained. The product was 110.1 mg; the molar yield was 97.4%.

Figure 9:
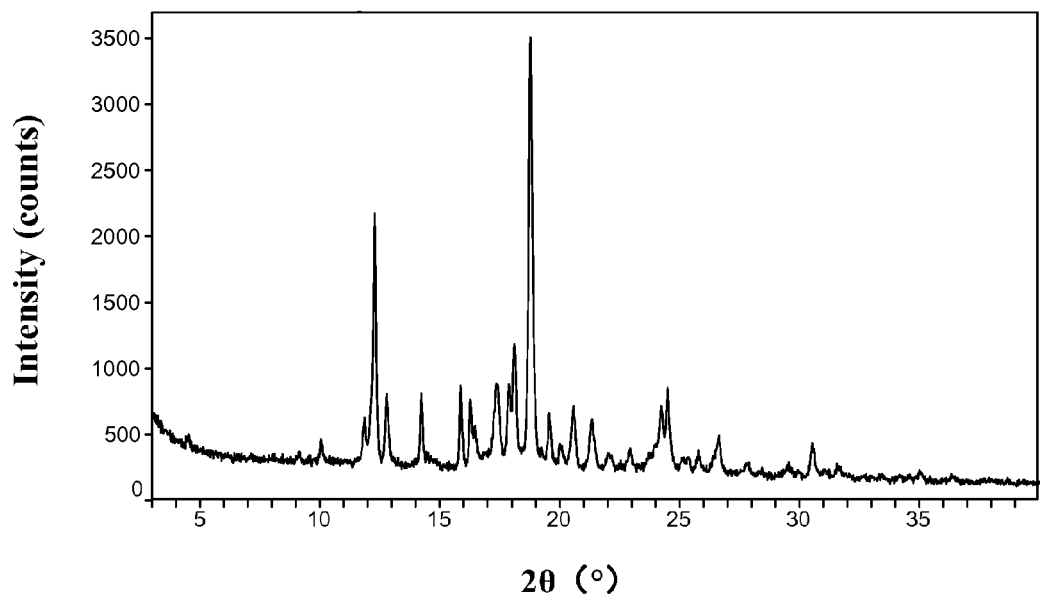
FIG. 9 is the XRPD pattern of Form III provided by the present invention
Figure 10:
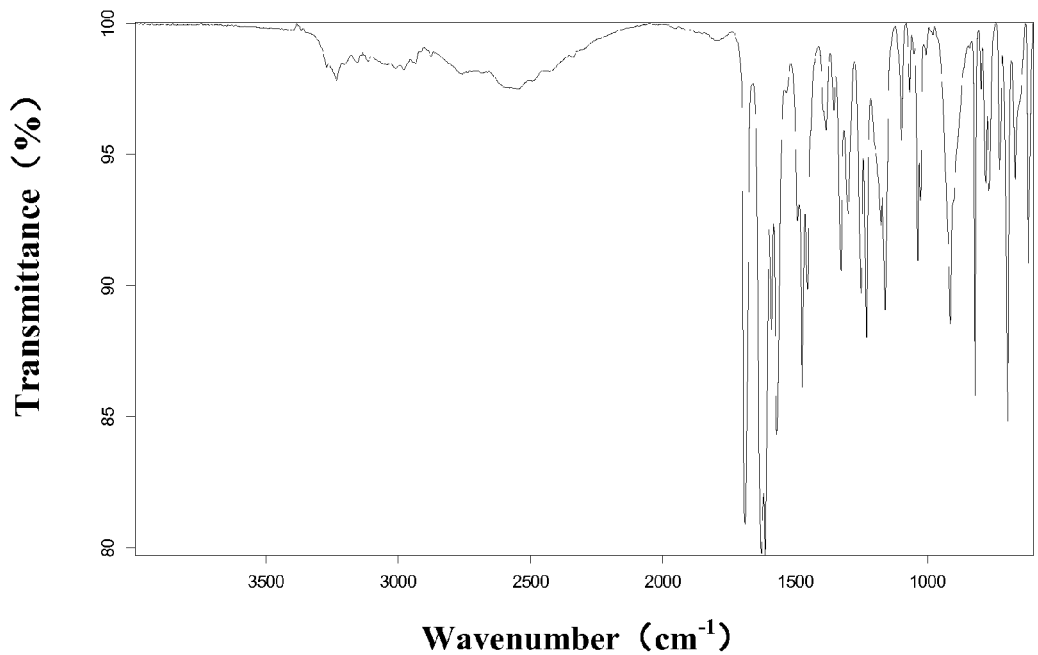
FIG. 10 is the IR spectrum of Form III provided by the present invention.
Figure 11:
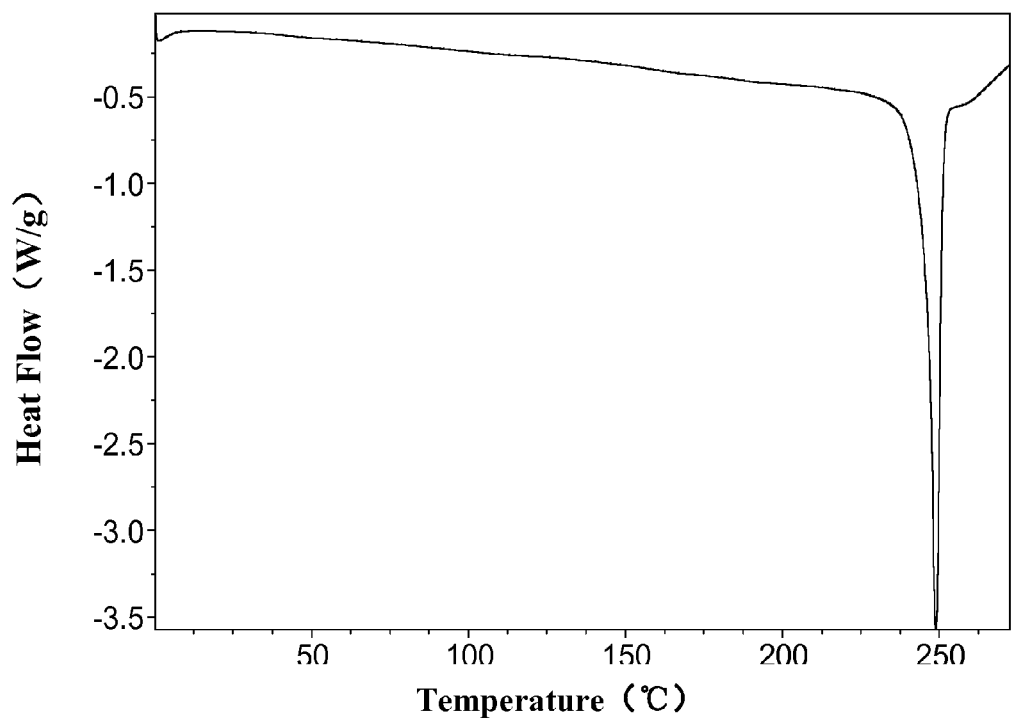
FIG. 11 is the DSC thermogram of Form III provided by the present invention.
Figure 12:
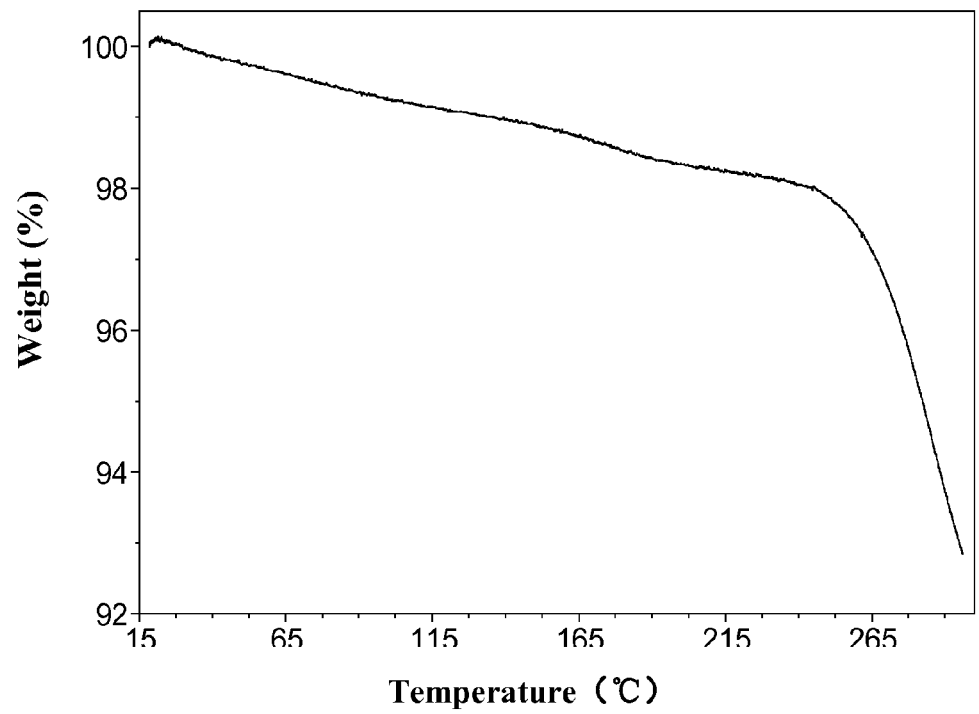
FIG. 12 is the TGA thermogram of Form III provided by the present invention.

The X-ray powder diffraction pattern is shown in FIG. 9.
The IR spectrum is shown in FIG. 10.
The DSC thermogram is shown in FIG. 11, indicating: the melting range was 244-249° C.
The TGA thermogram is shown in FIG. 12, indicating: a weight loss of about 1.1% occurred before 150° C. (anhydrate); the decomposition temperature was 265° C.
DVS indicates: the weight change within the relative humidity range of 20%-80% was 0.44%.

Example 9

To 105.9 mg of Form I of idelalisib in a 15 mL glass vial, 5 mL of acetone and 5 mL of water were added. A suspension was obtained after sonication for 5 min. The suspension was stirred at 40° C. for 3 days for crystallization. The obtained solid was filtered and dried under vacuum at 40° C. for 24 hours. Form III in the present invention was obtained. The product was 88.9 mg; the molar yield was 87.7%.

Example 10

To 112.5 mg of Form I of idelalisib in a 10 mL glass vial, 5 mL of nitromethane was added. A suspension was obtained after sonication for 5 min. The suspension was stirred at 0° C. for 14 days for crystallization. The obtained solid was filtered and dried under vacuum at 80° C. for 10 hours. Form III in the present invention was obtained. The product was 105.2 mg; the molar yield was 97.7%.

The XRPD patterns, IR spectra, DSC thermograms and TGA thermograms obtained from samples prepared in examples 9-10 were the same or similar as those obtained from the sample prepared in example 8, indicating the crystalline form obtained in examples 9-10 was the same as that obtained in example 8.

Example 11

3.28 mg of Form IX prepared in example 21 was studied by a DSC instrument following the procedures below: the sample was heated at a rate of 1° C./min to 150° C. and held for 1 min and then cooled naturally to room temperature. Form IV in the present invention was obtained. The product was 3.18 mg; the yield was 100%.

Figure 13:
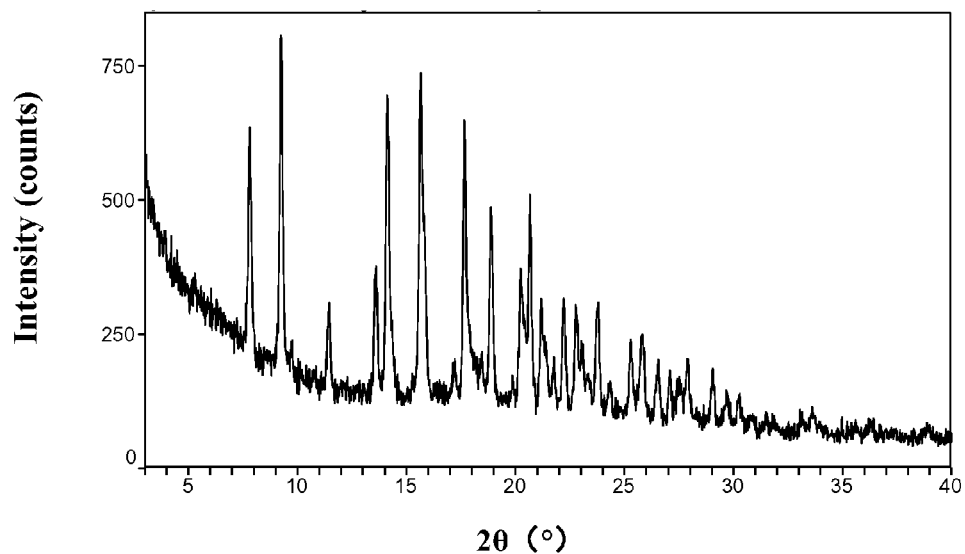
FIG. 13 is the XRPD pattern of Form IV provided by the present invention.
Figure 14:
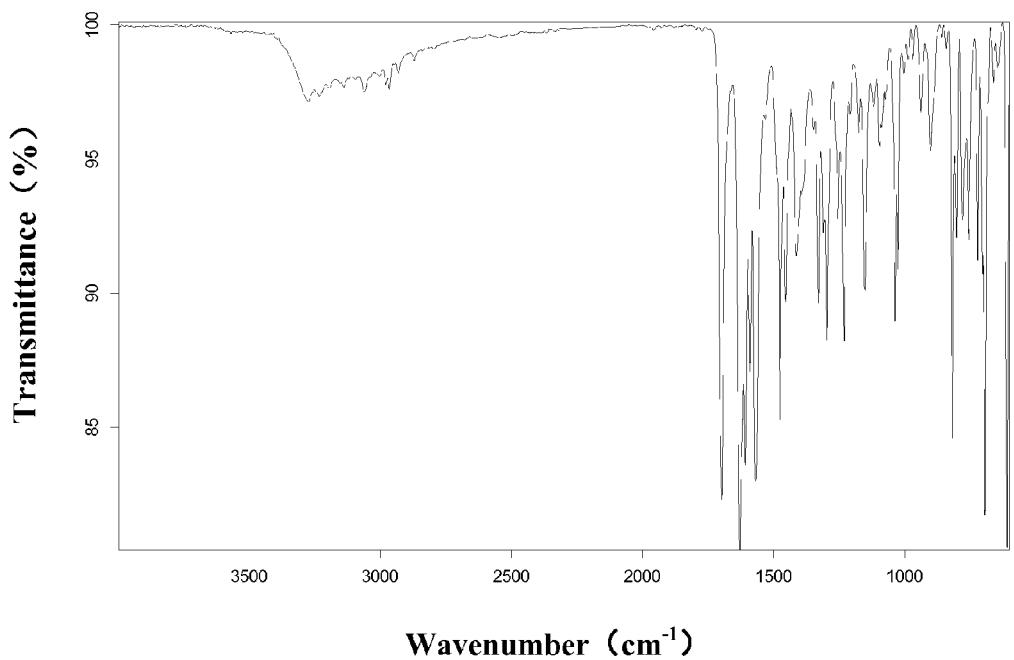
FIG. 14 is the IR spectrum of Form IV provided by the present invention.
Figure 15:
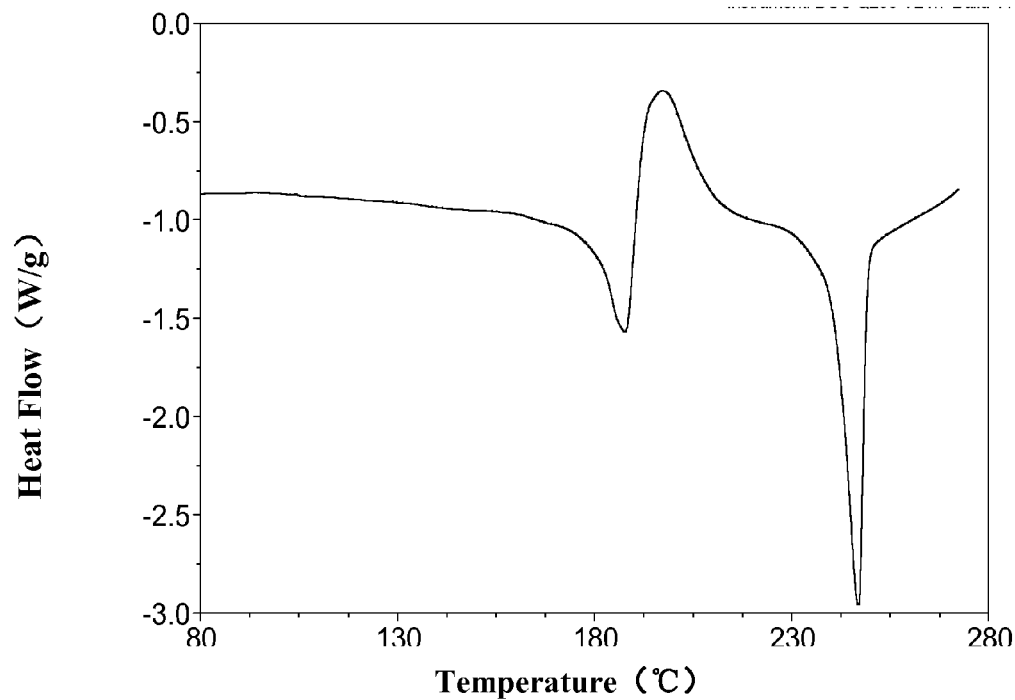
FIG. 15 is the DSC thermogram of Form IV provided by the present invention.
Figure 16:
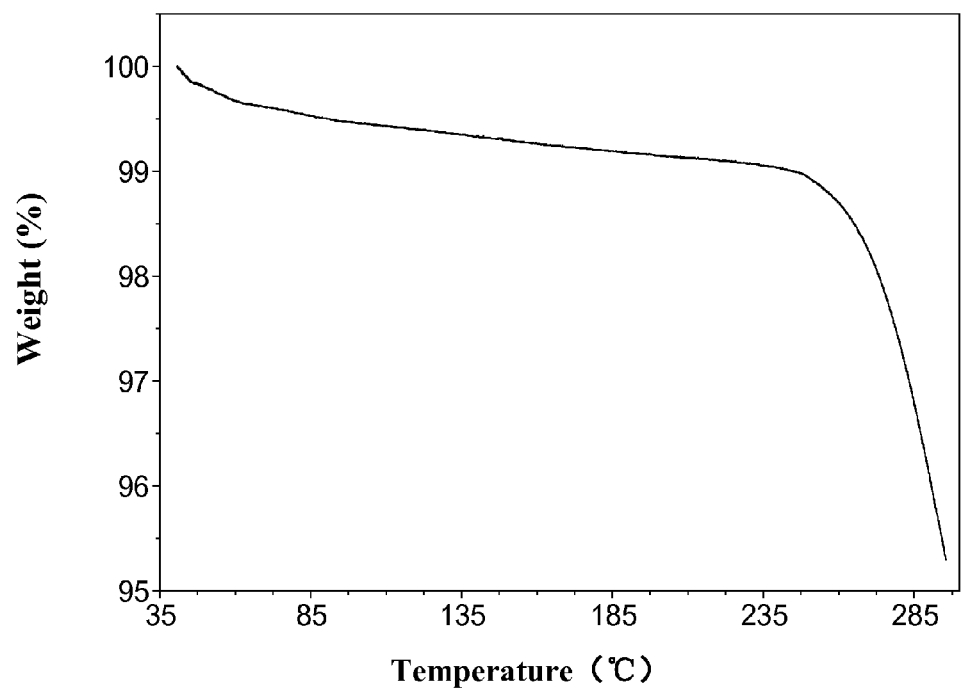
FIG. 16 is the thermogram of Form IV provided by the present invention.

The X-ray powder diffraction pattern is shown in FIG. 13.
The IR spectrum is shown in FIG. 14.
The DSC thermogram is shown in FIG. 15, indicating: the melting range was 180-188° C.; an exothermic form transformation peak was present at 190-219° C.; the melting range of the sample after the form transformation was 240-247° C.; after form transformation, Form II was formed.
The TGA thermogram is shown in FIG. 16, indicating: a weight loss of about 0.7% occurred before 150° C. (anhydrate); the decomposition temperature was 271° C.
DVS indicates: the weight change within the relative humidity range of 20%-80% was 0.27%.

Example 12

4.05 mg of Form IX prepared in example 21 was studied by a DSC instrument following the procedures below: the sample was heated at a rate of 15° C./min to 100° C. and held for 5 min and then cooled naturally to room temperature. Form IV in the present invention was obtained. The product was 3.93 mg; the yield was 100%.

Example 13

4.05 mg of Form IX prepared in example 21 was studied by a DSC instrument following the procedures below: the sample was heated at a rate of 10° C./min to 110° C. and held for 2 min and then cooled naturally to room temperature. Form IV in the present invention was obtained. The product was 3.93 mg; the yield was 100%.

The XRPD patterns, IR spectra, DSC thermograms and TGA thermograms obtained from samples prepared in examples 12-13 were the same or similar as those obtained from the sample prepared in example 11, indicating the crystalline form obtained in examples 12-13 was the same as that obtained in example 11.

Example 14

To 1.32 mg of Form I of idelalisib in a 5 mL glass vial, 1 mL of tetrahydrofuran was added. A suspension was obtained after sonication for 5 min. The suspension was stirred at room temperature for 8 days for crystallization. The obtained solid was filtered and dried in a blasting oven at 30° C. for 10 hours. Form V in the present invention was obtained. The product was 124.2 mg; the molar yield was 58%.

Figure 17:
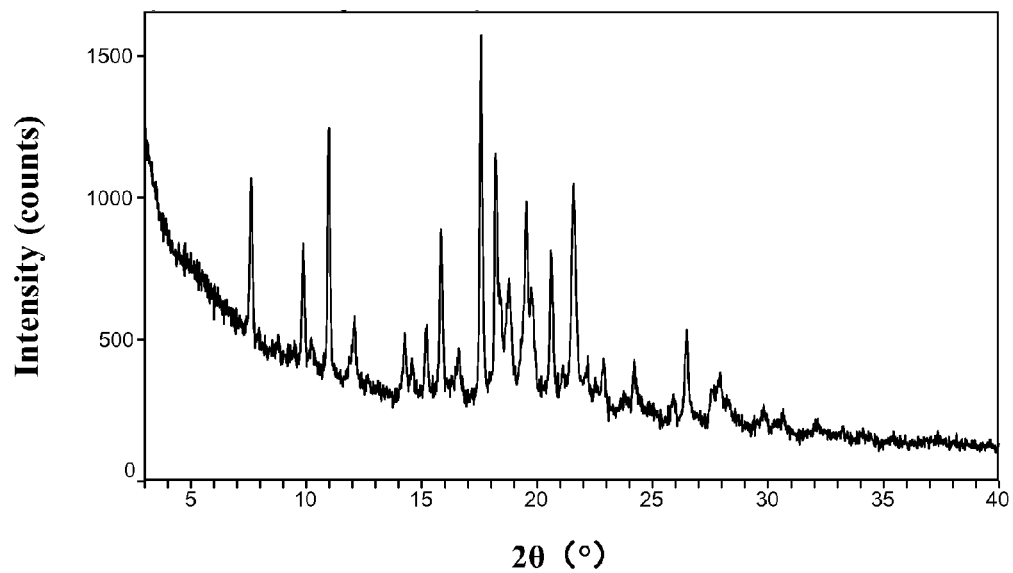
FIG. 17 is the XRPD pattern of Form V provided by the present invention.

The X-ray powder diffraction pattern is shown in FIG. 17.

Figure 18:
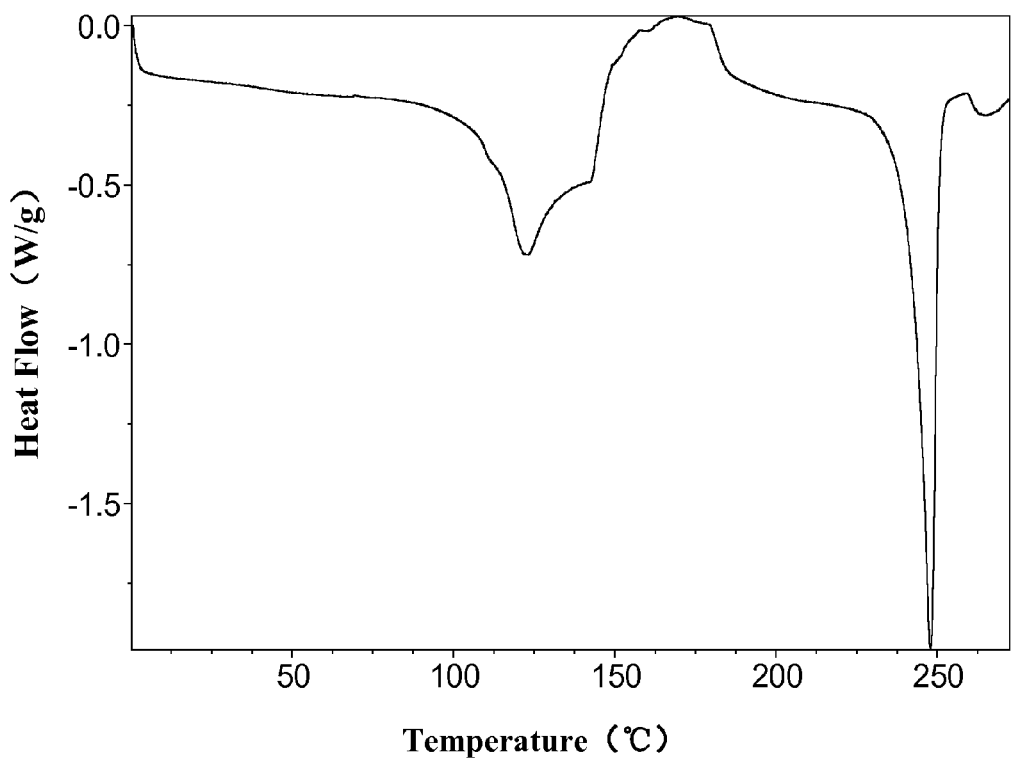
FIG. 18 is the DSC thermogram of Form V provided by the present invention.

The DSC thermogram is shown in FIG. 18, indicating: an endothermic desolvation peak was present at 93-142° C.; an exothermic form transformation peak was present at 142-187° C.; the melting range of the sample after the form transformation was 242-248° C.; after the form transformation, Form II was formed.

Figure 19:
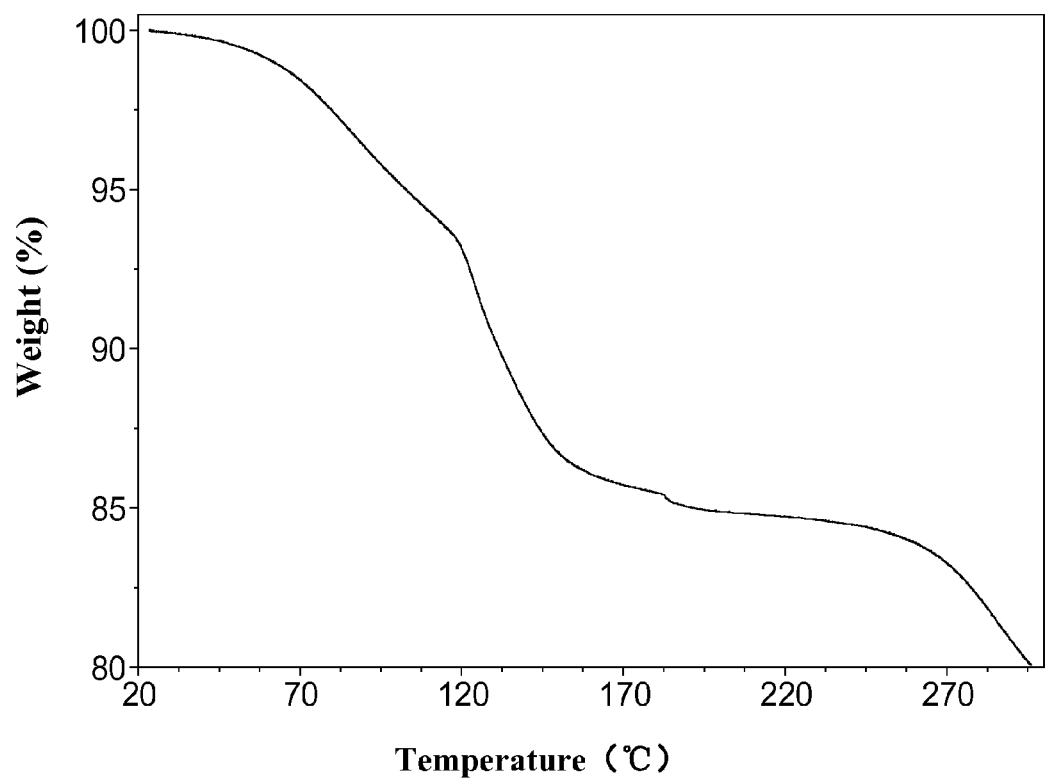
FIG. 19 is the TGA thermogram of Form V provided by the present invention.

The TGA thermogram is shown in FIG. 19, indicating: a weight loss of 15% occurred before 200° C. (1 idelalisib molecule per about 1 tetrahydrofuran molecule); the decomposition temperature was 264° C.

Example 15

To 90.12 mg of Form I of idelalisib in a 5 mL glass vial, 2 mL of water and 2 mL of isopropanol were added. A suspension was obtained after sonication for 5 min. The suspension was stirred at room temperature for 8 days for crystallization. The obtained solid was filtered and dried in a blasting oven at 60° C. for 10 hours. Form VI in the present invention was obtained. The product was 71.1 mg; the molar yield was 70.2%.

Figure 20:
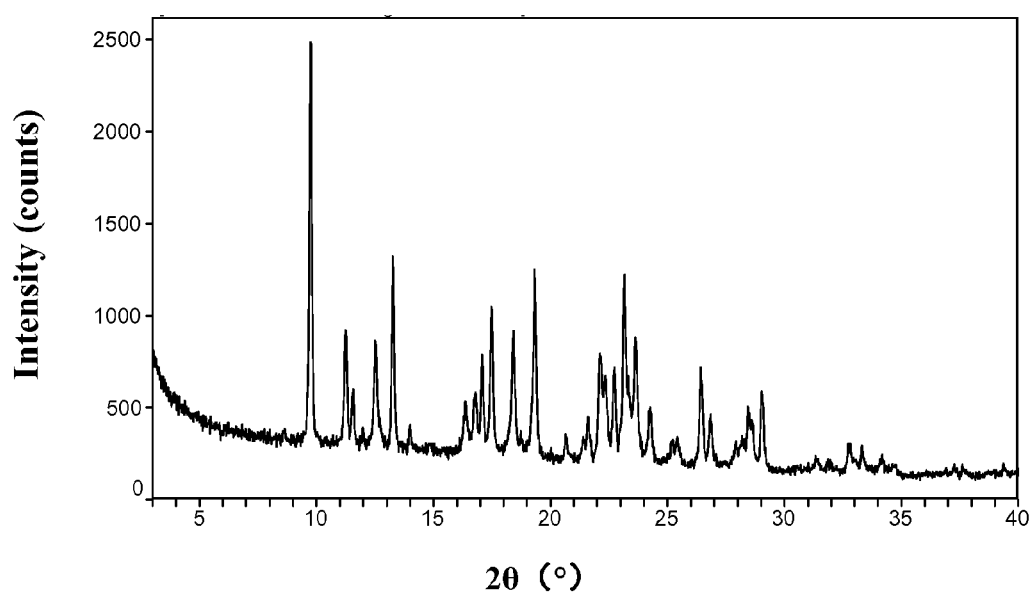
FIG. 20 is the XRPD pattern of Form VI provided by the present invention.
Figure 21:
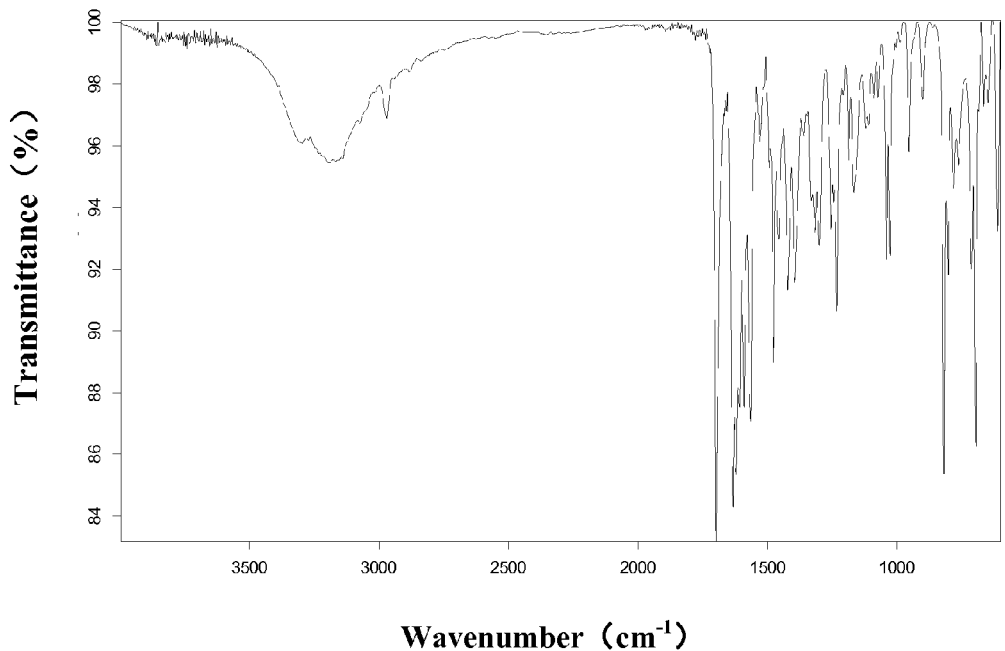
FIG. 21 is the IR spectrum of Form VI provided by the present invention.
Figure 22:
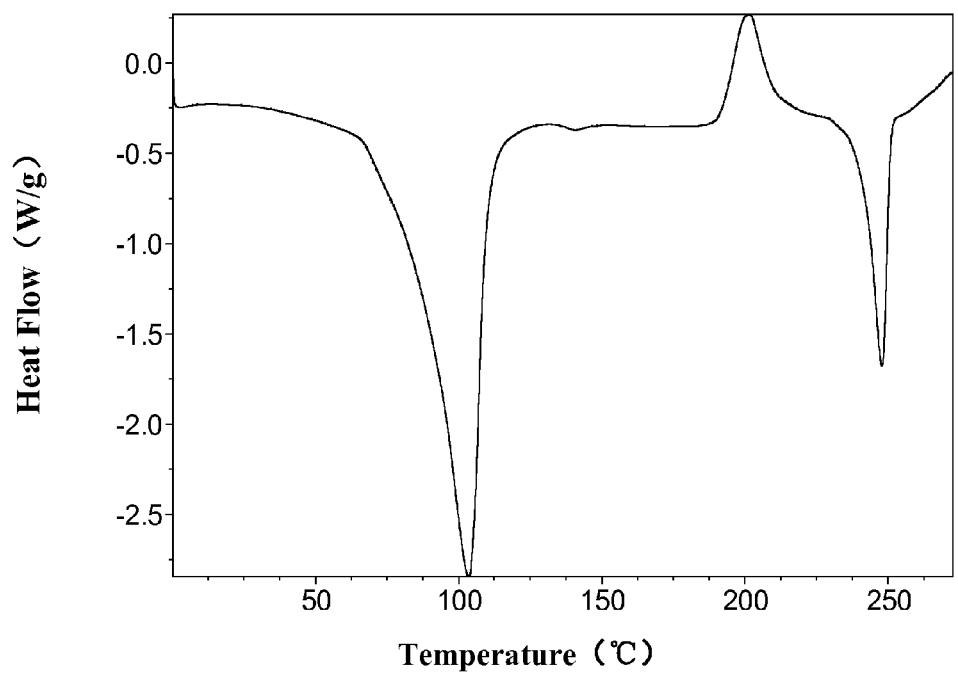
FIG. 22 is the DSC thermogram of Form VI provided by the present invention.

The X-ray powder diffraction pattern is shown in FIG. 20.
The IR spectrum is shown in FIG. 21.
The DSC thermogram is shown in FIG. 22, indicating: a broad endothermic peak (desolvation peak) was present at 60-126° C.; an exothermic form transformation peak was present at 187-221° C.; the melting range of the sample after the form transformation was 241-248° C.; after the form transformation, Form II was formed.

Figure 23:
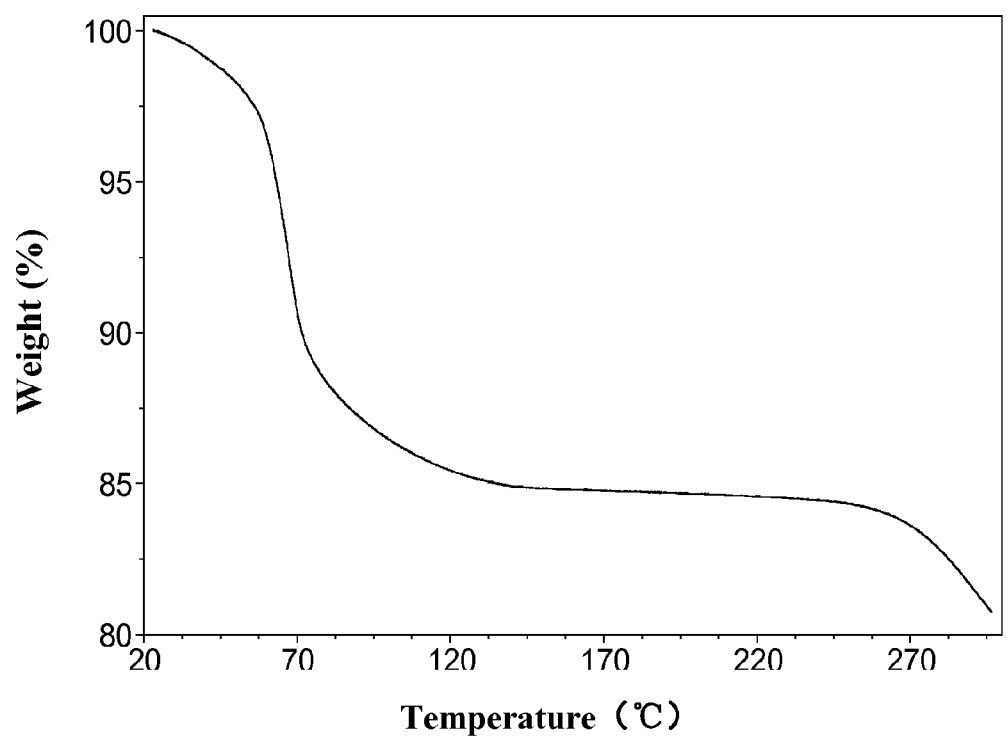
FIG. 23 is the TGA thermogram of Form VI provided by the present invention.

The TGA thermogram is shown in FIG. 23, indicating: a weight loss of about 15% occurred before 127.5° C. (1 idelalisib molecule is associated with about 4 water molecules); the decomposition temperature was 269° C.

DVS indicates: the weight change within the relative humidity range of 20%-80% was 0.57%.

Example 16

To 95.05 mg of Form I of idelalisib in a 10 mL glass vial, 5 mL of water and 2.5 mL of n-propanol were added. A suspension was obtained after sonication for 5 min. The suspension was stirred at room temperature for 8 days for crystallization. The obtained solid was filtered and dried in a blasting oven at 40° C. for 24 hours. Form VI in the present invention was obtained. The product was 76.0 mg; the molar yield was 71.2%.

The XRPD pattern, IR spectrum, DSC thermogram and TGA thermogram obtained from the sample prepared in example 16 were the same or similar as those obtained from the sample prepared in example 15, indicating the crystalline form obtained in example 16 was the same as that obtained in example 15.

Example 17

To 98.52 mg of Form I of idelalisib in a 10 mL glass vial, 6 mL of methyl tert-butyl ether was added. A suspension was obtained after sonication for 5 min. The suspension was stirred at room temperature for 8 days for crystallization. The obtained solid was filtered and dried in a blasting oven at 40° C. for 24 hours. Form VII in the present invention was obtained. The product was 92.9 mg; the molar yield was 89%.

Figure 24:
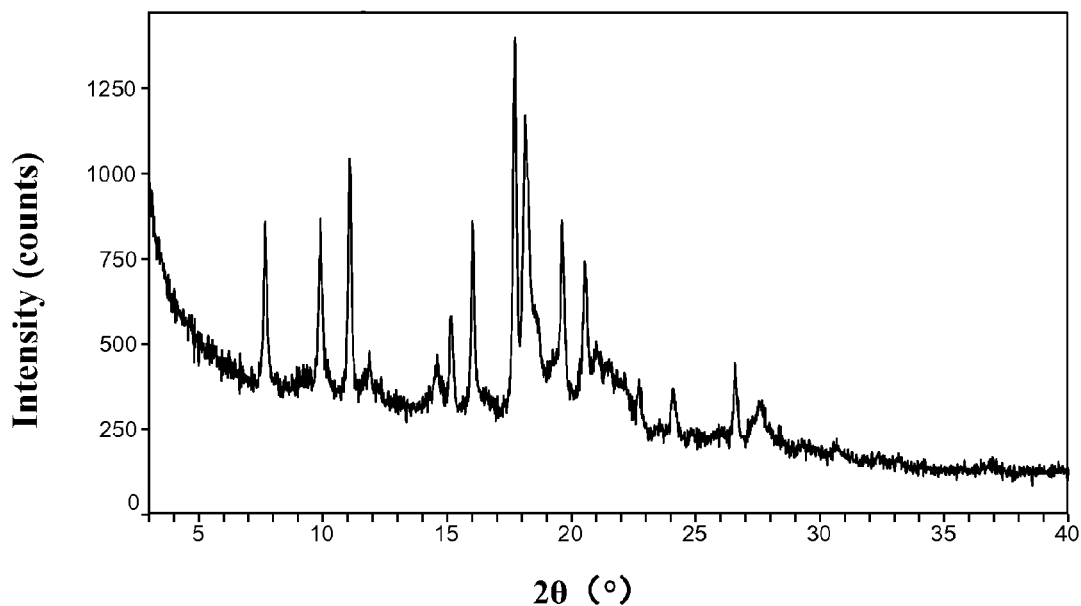
FIG. 24 is the XRPD pattern of Form VII provided by the present invention.
Figure 25:
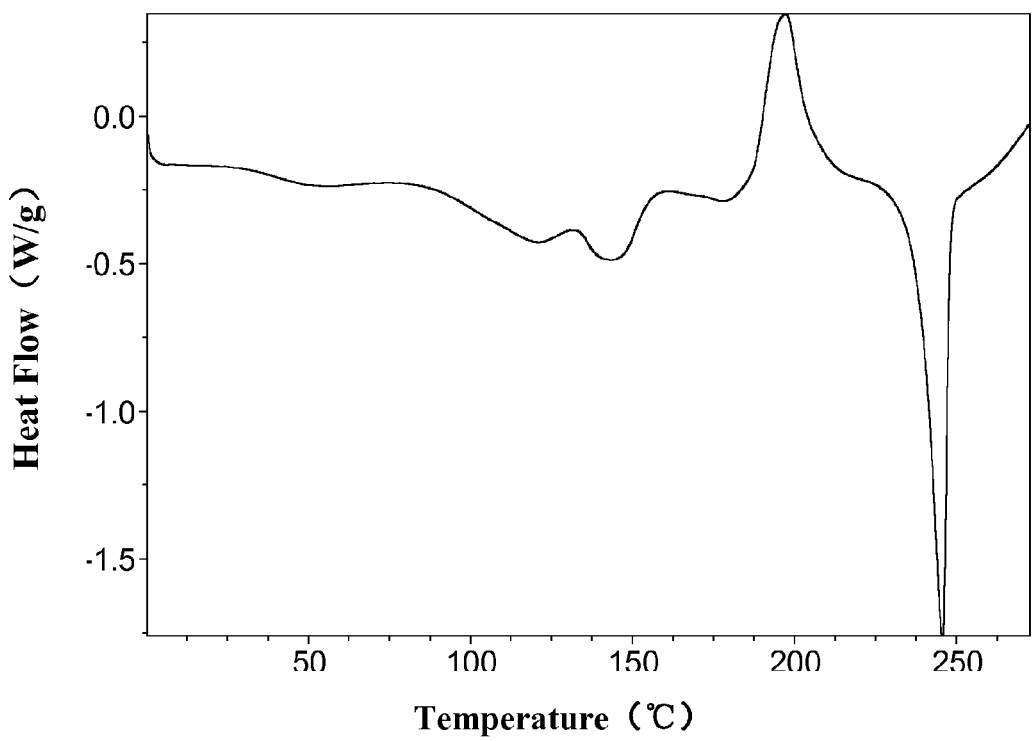
FIG. 25 is the DSC thermogram of Form VII provided by the present invention.

The X-ray powder diffraction pattern is shown in FIG. 24.
The DSC thermogram is shown in FIG. 25, indicating: a broad endothermic peak (i.e. desolvation) was present at 82-132° C.; melting occurred at 132-160° C., and an exothermic peak (i.e. form transformation) was present at 180-220° C., followed by melting at 238-246° C.; after the form transformation, Form II was formed.

Figure 26:
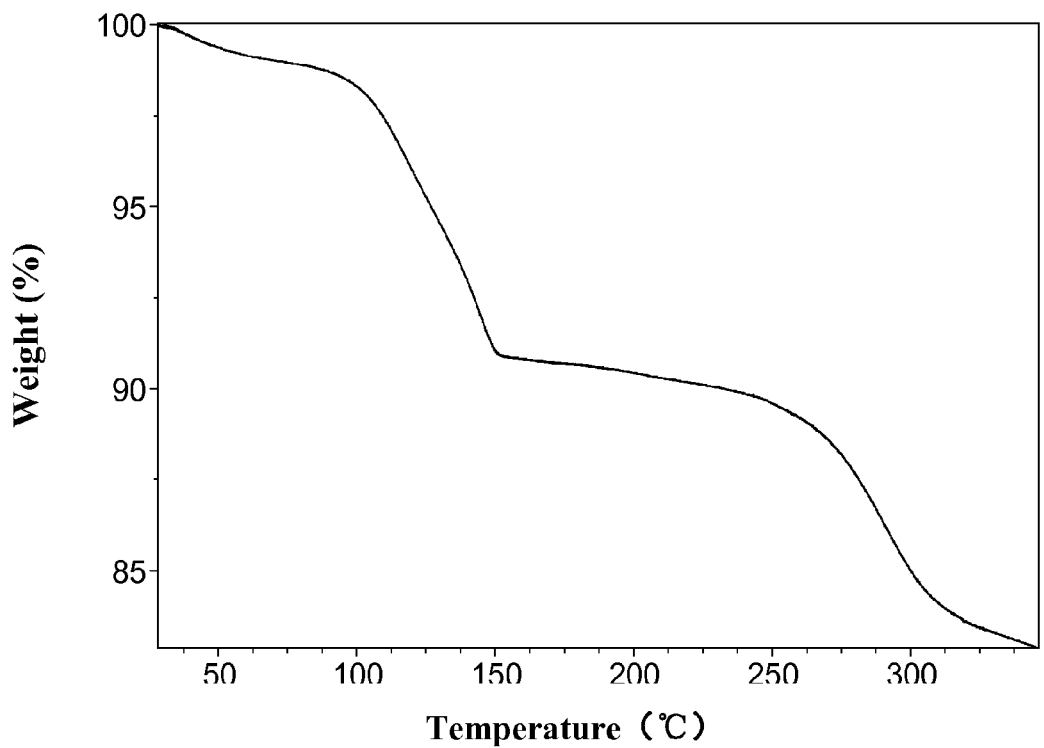
FIG. 26 is the TGA thermogram of Form VII provided by the present invention.

The TGA thermogram is shown in FIG. 26, indicating: a weight loss of 9.1% occurred before 150° C. (methyl tert-butyl ether solvate, about 0.5 methyl tert-butyl ether molecule associated with 1 idelalisib molecule); the decomposition temperature was 267° C.

Example 18

4.87 mg of Form X of idelalisib prepared in example 26 was studied by a DSC instrument following the procedures below: the sample was heated at a rate of 1° C./min to 150° C. and held for 5 min and then cooled naturally to room temperature. Form VIII in the present invention was obtained. The product was 4.16 mg; the molar yield was 100%.

Figure 27:
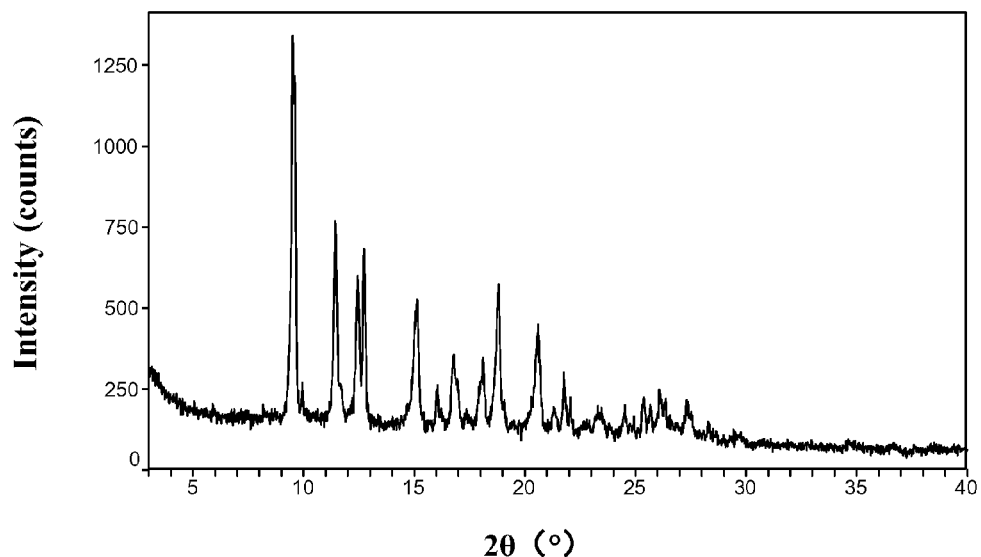
FIG. 27 is the XRPD pattern of Form VIII provided by the present invention.
Figure 28:
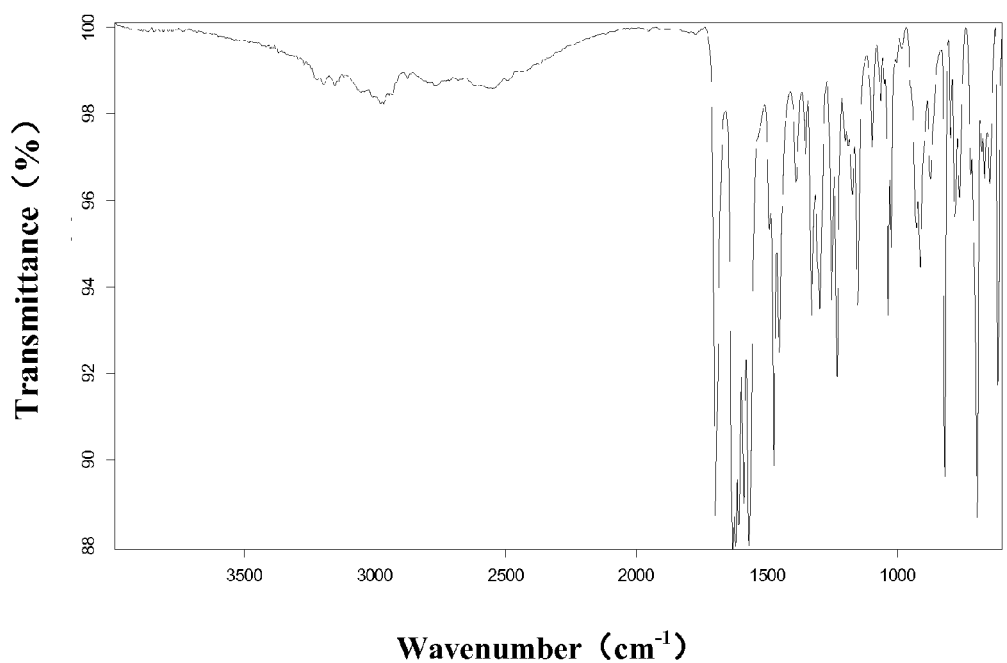
FIG. 28 is the IR spectrum of Form VIII provided by the present invention.
Figure 29:
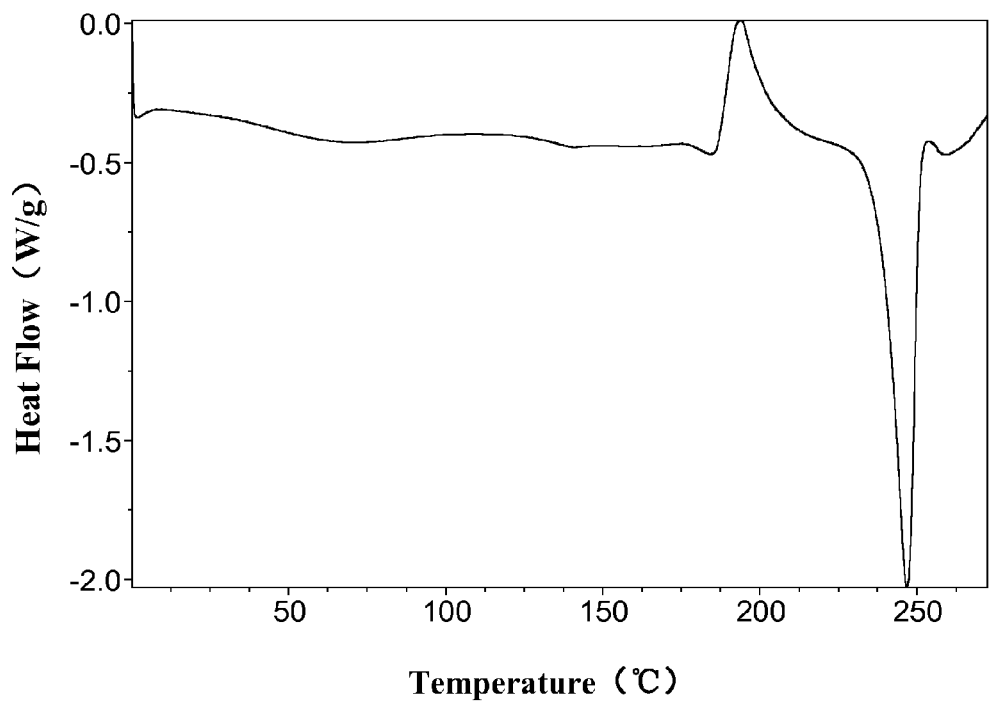
FIG. 29 is the DSC thermogram of Form VIII provided by the present invention.

The X-ray powder diffraction pattern is shown in FIG. 27.
The IR spectrum is shown in FIG. 28.
The DSC thermogram is shown in FIG. 29, indicating: an exothermic form transformation peak was present at 184-218° C.; the melting range of the sample after the form transformation was 239-247° C.; after the form transformation, Form II was formed.

Figure 30:
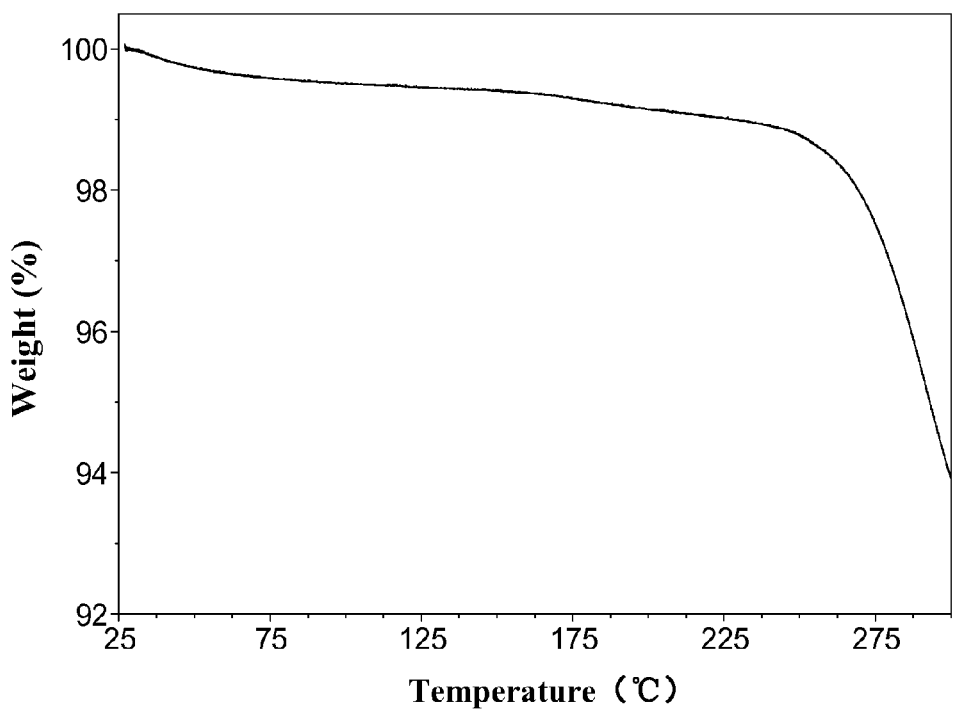
FIG. 30 is the TGA thermogram of Form VIII provided by the present invention.

The TGA thermogram is shown in FIG. 30, indicating: a weight loss of about 0.59% occurred before 150° C. (anhydrate); the decomposition temperature was 270° C.

DVS indicates: the weight change within the relative humidity range of 20%-80% was 0.84%.

Example 19

4.87 mg of Form X of idelalisib prepared in example 26 was studied by a DSC instrument following the procedures below: the sample was heated at a rate of 15° C./min to 200° C. and held for 1 min and then cooled naturally to room temperature. Form VIII in the present invention was obtained. The product was 4.16 mg; the molar yield was 100%.

Example 20

4.87 mg of Form X of idelalisib prepared in example 26 was studied by a DSC instrument following the procedures below: the sample was heated at a rate of 10° C./min to 175° C. and held for 2 min and then cooled naturally to room temperature. Form VIII in the present invention was obtained. The product was 4.16 mg; the molar yield was 100%.

The XRPD patterns, IR spectra, DSC thermograms and TGA thermograms obtained from the samples prepared in examples 19-20 were the same or similar as those obtained from the sample prepared in example 18, indicating the crystalline form obtained in examples 19-20 was the same as that obtained in example 18.

Example 21

To 95.88 mg of Form I of idelalisib in a 5 mL glass vial, 3 mL of water and 0.75 mL of ethanol were added. A suspension was obtained after sonication for 5 min. The suspension was stirred at room temperature for 8 days for crystallization. The obtained solid was filtered and dried under vacuum at 40° C. for 24 hours. Form IX in the present invention was obtained. The product was 60.2 mg; the molar yield was 63.6%.

Figure 31:
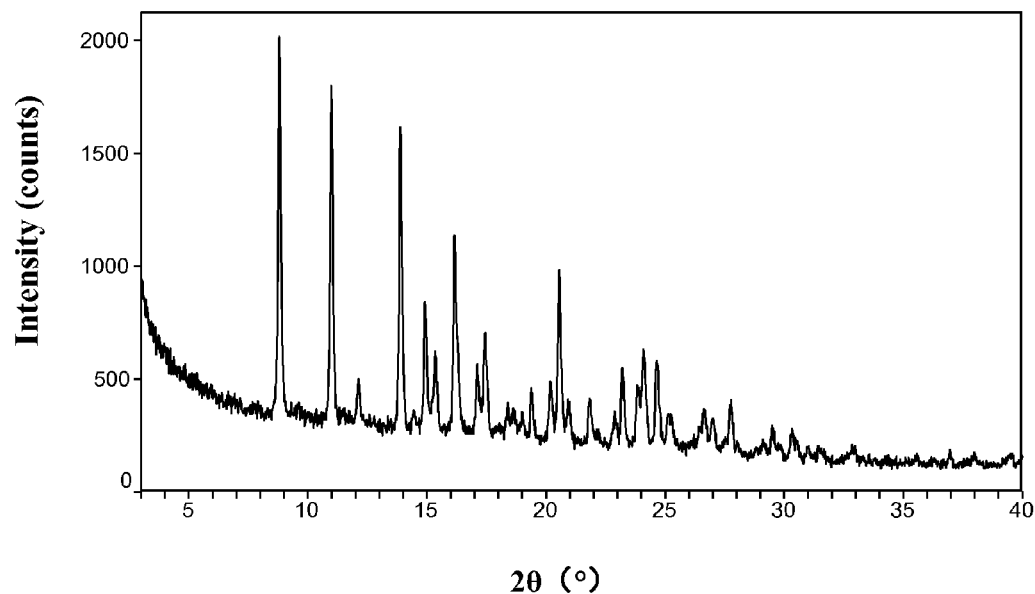
FIG. 31 is the XRPD pattern of Form IX provided by the present invention.
Figure 32:
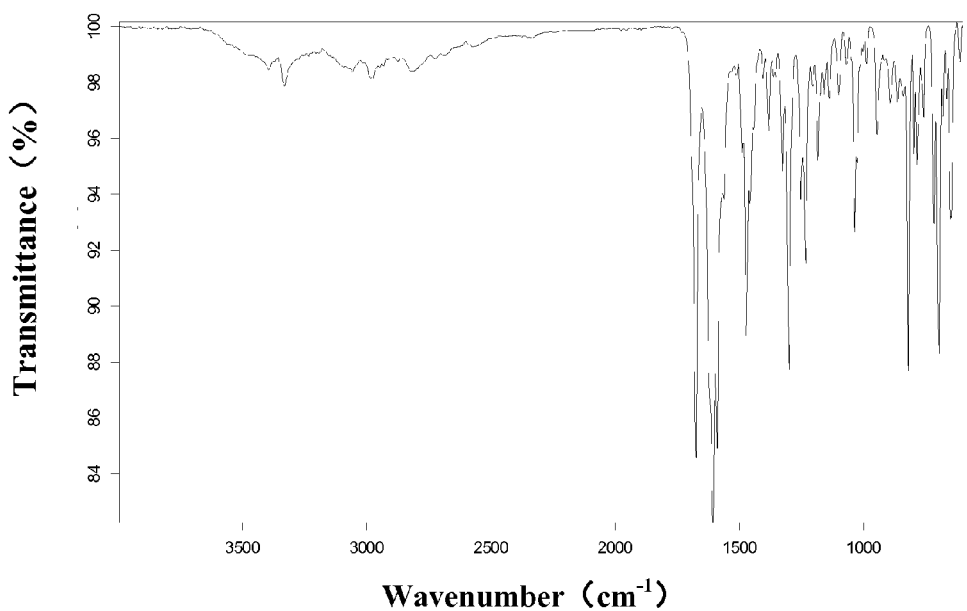
FIG. 32 is the IR spectrum of Form IX provided by the present invention.
Figure 33:
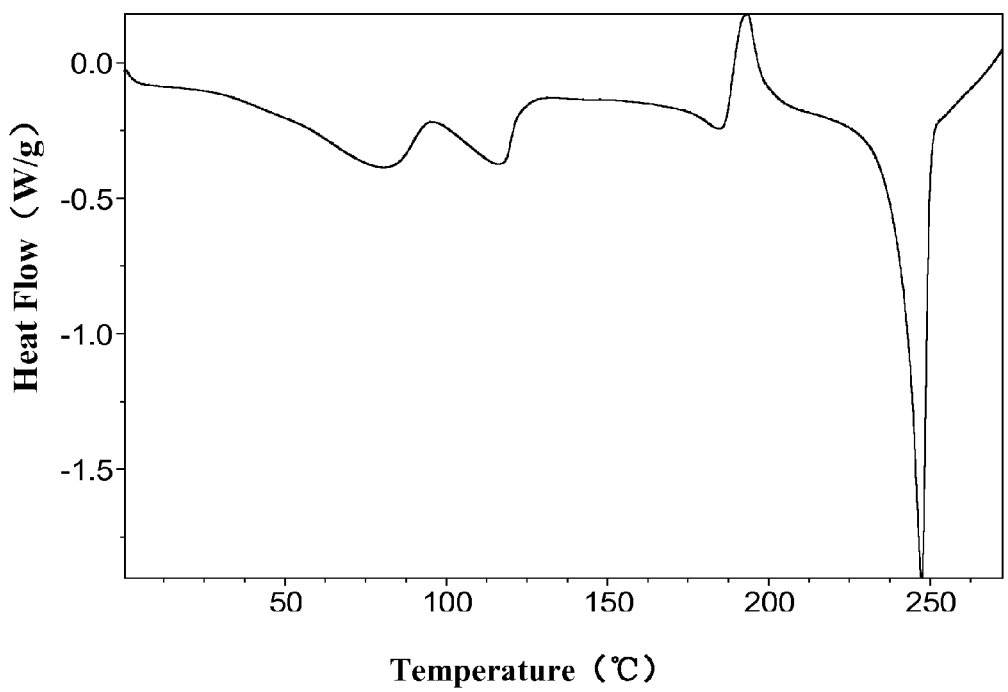
FIG. 33 is the DSC thermogram of Form IX provided by the present invention.
Figure 34:
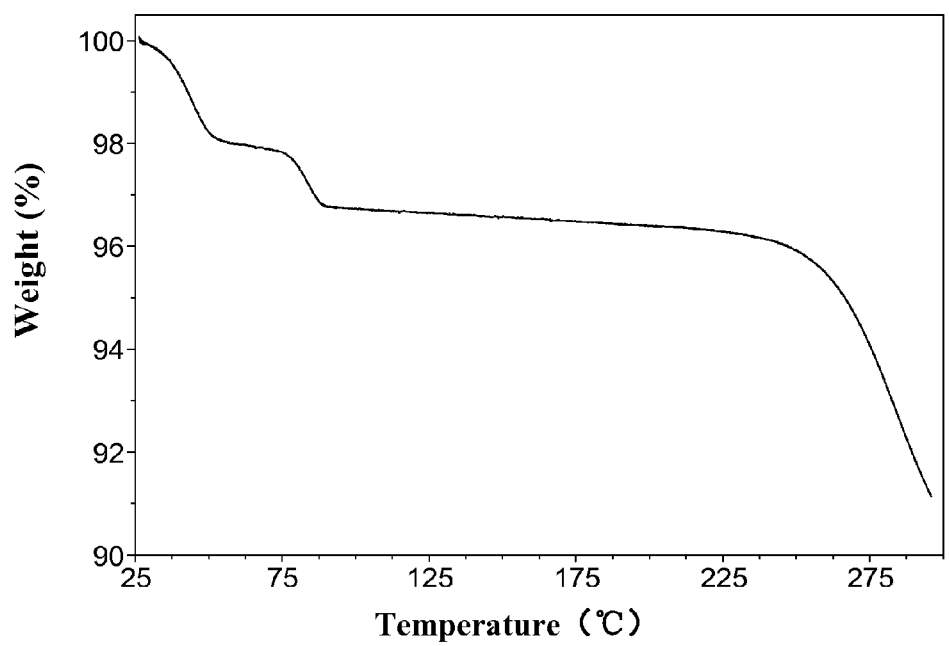
FIG. 34 is the TGA thermogram of Form IX provided by the present invention.

The X-ray powder diffraction pattern is shown in FIG. 31.
The IR spectrum is shown in FIG. 32.
The DSC thermogram is shown in FIG. 33, indicating: two endothermic peaks (i.e. desolvation) were present at 37-96° C. and 96-128° C.; an exothermic (form transformation) peak was present at 184-210° C.; the melting range of the sample after the form transformation was 241-247° C.; after the form transformation, Form II was formed.
The TGA thermogram is shown in FIG. 34, indicating: a weight loss of about 3.3% occurred before 100° C. (associated with about 0.7 water molecule); the decomposition temperature was 261° C.
DVS indicates: the weight change within the relative humidity range of 20%-80% was 0.3%.

Example 22

To 48.0 mg of Form I of idelalisib in a 1.0 mL glass vial, 3 mL of water and 3 mL of ethanol were added. A suspension was obtained after sonication for 5 min. The suspension was stirred at room temperature for 8 days for crystallization. The obtained solid was filtered and dried under vacuum at 40° C. for 24 hours. Form IX in the present invention was obtained. The product was 25.0 mg; the molar yield was 52.8%.

Example 23

To 100.0 mg of Form I of idelalisib in a 50 mL glass vial, 30 mL of water and 3 mL of ethanol were added. A suspension was obtained after sonication for 5 min. The suspension was stirred at room temperature for 8 days for crystallization. The obtained solid was filtered and dried under vacuum at 40° C. for 24 hours. Form IX in the present invention was obtained. The product was 58.9 mg; the molar yield was 59.7%.

Example 24

To 100.0 mg of Form I of idelalisib in a 50 mL glass vial, 12 mL of water and 3 mL of ethanol were added to form a suspension. The suspension was sonicated at room temperature at a frequency of 40 Khz for 1 hour. The obtained solid was filtered and dried under vacuum at 40° C., for 24 hours. Form IX in the present invention was obtained. The product was 67.2 mg; the molar yield was 68.2%.

Example 25

To 19.2 mg of Form I of idelalisib in a 50 mL glass vial, 12 mL of water and 3 mL of ethanol were added to produce a suspension. The suspension was sonicated at room temperature at a frequency of 20 Khz for 3 hours. The obtained solid was filtered and dried under vacuum at 40° C. for 24 hours. Form IX in the present invention was obtained. The product was 12.3 mg; the molar yield was 64.8%.

The XRPD patterns, IR spectra, DSC thermograms and TGA thermograms obtained from the samples prepared in examples 22-25 were the same or similar as those obtained from the sample prepared in example 21, indicating the crystalline form obtained in examples 22-25 was the same as that obtained in example 21.

Example 26

Figure 35:
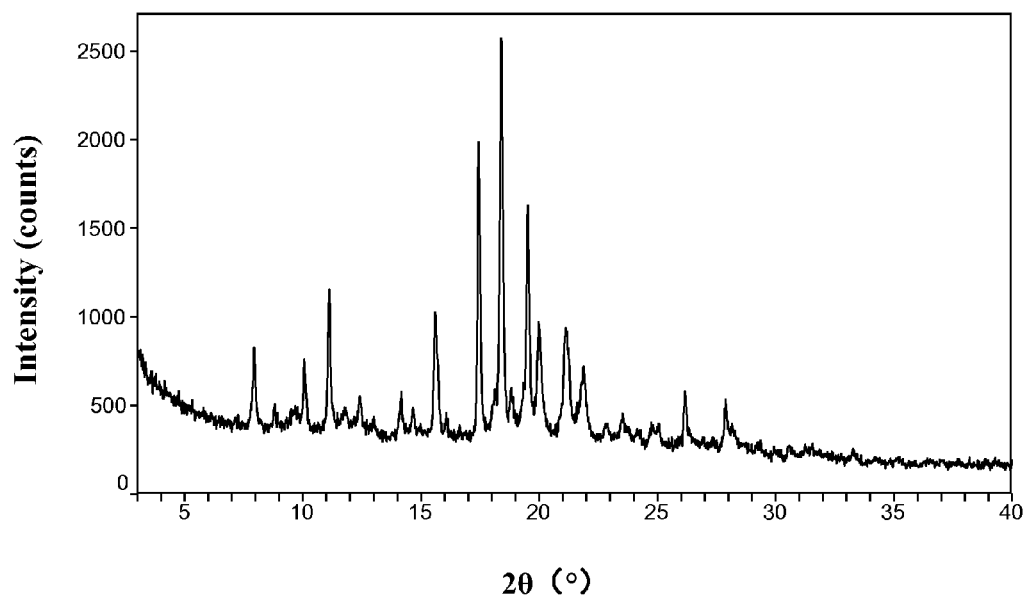
FIG. 35 is the XRPD pattern of Form X provided by the present invention.
Figure 36:
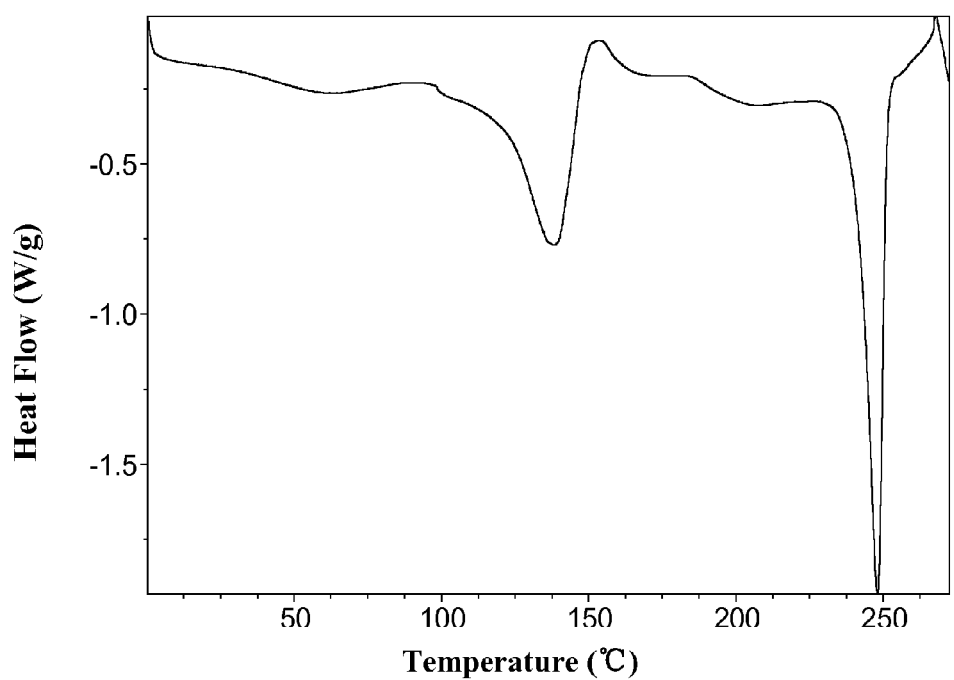
FIG. 36 is the DSC thermogram of Form X provided by the present invention.

To 80.21 mg of Form I of idelalisib in a 50 mL glass vial, 10 mL of dioxane was added. A suspension was obtained after sonication for 5 min. The suspension was stirred at room temperature for 8 days for crystallization. The obtained solid was filtered and dried under vacuum at 40° C. for 24 hours. Form X in the present invention was obtained. The product was 75.6 mg; the molar yield was 84.2%.
The X-ray powder diffraction pattern is shown in FIG. 35.
The DSC thermogram is shown in FIG. 36, indicating: an broad endothermic peak desolvation) was present at 94-153° C.; the melting range after desolvation was 241-248° C.

Figure 37:
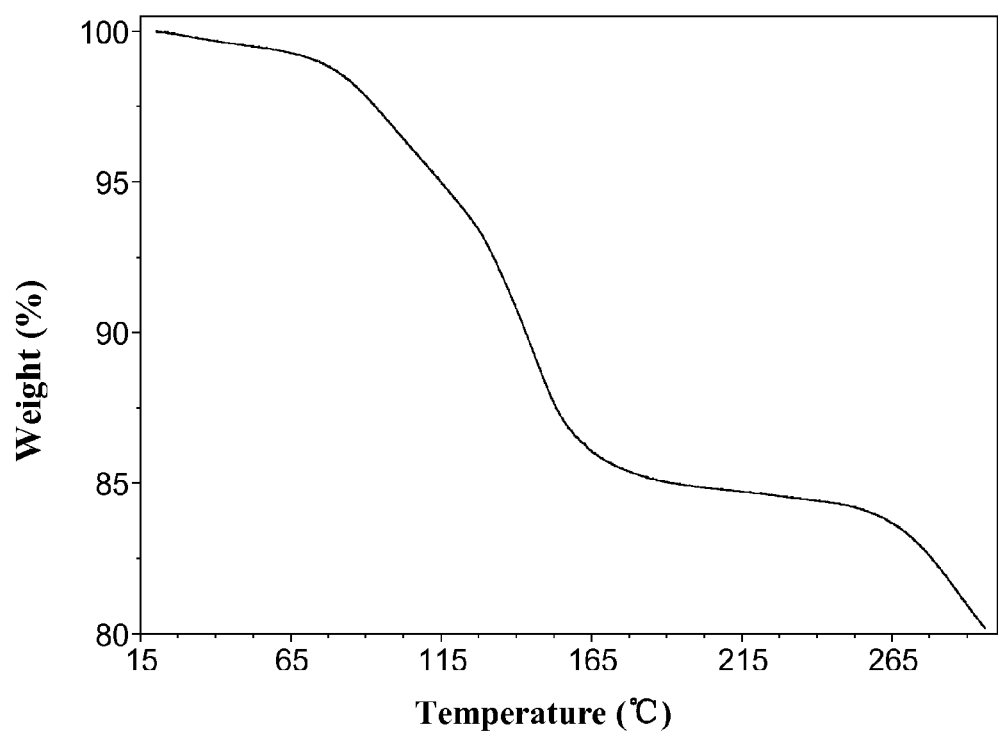
FIG. 37 is the TGA thermogram of Form X provided by the present invention.

The TGA thermogram is shown in FIG. 37, indicating: a weight loss of about 15% occurred before 200° C. (dioxane solvate, with 1 idelalisib molecule associated with about 0.8 dioxane molecule); the decomposition temperature was 267° C.

Example 27

Idelalisib tablets were prepared using Form II as the active ingredient. See Table 1 for the formula of said tablets.

TABLE 1

Formula of tablets of idelalisib Form II

| Components | Content (mg/tablet) | Weight percent (%) |
|---|---|---|
| Form II of idelalisib in the present invention | 10 | 3.33 |
| Pregelatinized starch | 272.5 | 90.84 |
| Polyvinyl pyrrolidone | 10 | 3.33 |
| Croscarmellose sodium | 6 | 2.00 |
| Magnesium stearate | 1.5 | 0.50 |
| Tablets | 300 | 100 |

The tablets were prepared by the following procedure: mix Form II of idelalisib in the present invention and pregelatinized starch to obtain a well-mixed powder mixture; dissolve polyvinyl pyrrolidone in 60% ethanol solution, add the resulting solution to the mixed powder mixture to produce a soft material; pass the soft material through a 30-mesh sieve for granulation, dry granules at 50-75° C., add croscarmellose sodium and magnesium stearate to the dry granules, mix and perform tabletting.

Examples 28-35

Using the same procedures in example 27, and replacing Form II in example 27 with Form III, Form IV, Form V, Form VI, Form VII, Form VIII, Form IX and Form X of idelalisib, respectively, to obtain idelalisib tablets with Form III, Form IV, Form V, Form VI, Form VII, Form VIII, Form IX and Form X as the crystalline forms of the active ingredient.

Example 36

Idelalisib capsules were prepared using Form II as the active ingredient. See Table 2 for the formula of said capsules.

TABLE 2

Formula of capsules of idelalisib Form II

| Components | Content (mg/capsule) | Weight percent (%) |
|---|---|---|
| Form II of idelalisib in the present invention | 10 | 6.67 |
| Lactose | 128.5 | 85.66 |
| Polyvinyl pyrrolidone | 10 | 6.67 |
| Micronized silica gel | 1.5 | 1.00 |
| Capsules | 150 | 100 |

The capsules were prepared by the following procedures: mix Form II of idelalisib in the present invention with lactose to obtain a well-mixed powder mixture; dissolve polyvinyl pyrrolidone in 60% ethanol aqueous solution; add the resulting solution to the powder mixture to produce a soft material; pass the soft material through a 30-mesh sieve for granulation, dry granules at 50-75° C., add micronized silica gel to the dry granules, mix and fill into gelatin capsules.

Example 37-44

Using the same procedures in example 36, and replacing Form II in example 36 with Form III, Form IV, Form V, Form VI, Form VII, Form VIII, Form IX and Form X of idelalisib, respectively, to obtain idelalisib capsules with Form III, Form IV, Form V, Form VI, Form VII, Form VIII, Form IX and Form X as the crystalline forms of the active ingredient.

Example 45

Different crystalline forms of idelalisib were compared in terms of stability (including storage stability, competitive slurry) and hygroscopicity. See Table 3 for the results.

Samples were Form II prepared in example 2, Form III prepared in example 8, Form IV prepared in example 11, Form V prepared in example 14, Form VI prepared in example 15, Form VII prepared in example 17, Form VIII prepared in example 18, Form IX prepared in example 21, Form X prepared in example 26 and the known Form I prepared in example 1. The operating procedures are detailed below:

Storage stability test: samples were stored at 25° C. and 60% RH for 3 months, and XRPD patterns before and after storage were compared.

Competitive slurry ①: suspensions of an equal quantity (5 mg) of Form I, Form II, Form III, Form IV and Form VIII in of nitromethane (no solvate formation in the solvent system) were stirred at room temperature tier 7 days and then the solids were subjected to XRPD characterization.

Competitive slurry ②: suspensions of an equal quantity (5 mg) of Form VI and Form IX in 1 mL of mixed solvent of isopropanol and water (1:4, v/v) (no solvate formation in the solvent system) were stirred at room temperature for 7 days and then the solids were subjected to XRPD characterization.

Hygroscopicity comparison: DVS isothermal sorption curves were used, and weight changes within the 20%-80% RH range were measured.

It can be known from Table 3 that: (1) regarding storage stability, Form II, Form III, Form IV, Form V, Form VI, Form VII, Form VIII, Form IX and Form X in the present invention and the known Form I all are stable during storage; (2) regarding competitive slurries, through the competitive slurry in nitromethane, Form I, Form II, Form IV and Form VIII in the present invention all transformed into Form III, while Form III remained unchanged, indicating Form III is the most stable form in nitromethane; through the competitive slurry in the mixed solvent of isopropanol and water, Form IX transformed into Form VI, while Form VI remained unchanged, indicating Form VI is stable in the mixed solvent of isopropanol and water; and (3) regarding hygroscopicity, Form II, Form III, Form IV, Form VI, Form VIII and Form IX in the present invention are all less hygroscopic than the known Form I, wherein Form IV and Form IX have the least hygroscopicity.

Example 46

Form I and Form IX of idelalisib were compared in stability (including storage stability and competitive slurry). See Table 4 for the results.

Samples were from Form IX prepared in example 21 and Form I prepared in example 1, respectively. The operating procedures are detailed below:

Storage stability test: samples were stored at 25° C. and 60% RH for 6 months, and XRPD patterns before and after storage were compared.

Competitive slurry: suspensions of an equal quantity (4 mg) of Form IX and Form I in 1 mL of mixed solvents of ethanol and water at different volume ratios (1:1, 1:4, 1:5 and 1:10) were stirred at room temperature for 7 days and then the solids were subjected to XRPD characterization.

TABLE 3

Comparison of different polymorphic forms of idelalisib

| Polymorphic form | Stability | | Weight change within 20%-80% RH range (%) |
|---|---|---|---|
| | Storage stability | Competitive slurry | |
| I | The original crystal form remained unchanged | Competitive slurry ①: In nitromethane, Form I, Form II, Form IV and Form VIII all transformed into Form III, while Form III remained unchanged. Competitive slurry ②: In the mixed solvent of isopropanol and water, Form IX transformed into Form VI, while Form VI remained unchanged. | 0.95 |
| II | The original crystal form remained unchanged | | 0.46 |
| III | The original crystal form remained unchanged | | 0.44 |
| IV | The original crystal form remained unchanged | | 0.27 |
| V | The original crystal form remained unchanged | | Not measured |
| VI | The original crystal form remained unchanged | | 0.57 |
| VII | The original crystal form remained unchanged | | Not measured |
| VIII | The original crystal form remained unchanged | | 0.84 |
| IX | The original crystal form remained unchanged | | 0.3 |
| X | The original crystal form remained unchanged | | Not measured |

TABLE 4

Comparison of Form I and Form IX

| Polymorphic form | Stability | |
|---|---|---|
| | Storage stability | Competitive slurry |
| I | The original crystal form remained unchanged | In the mixed solvents of ethanol and water, Form IX remained unchanged, while Form I transformed into Form IX in the present invention. |
| IX | The original crystal form remained unchanged | |

It can be known from Table 4 that: (1) regarding storage stability, both Form IX in the present invention and Form I kept stable during storage; (2) through the competitive slurry in the mixed solvents of ethanol and water, Form IX remained unchanged, while Form I transformed into Form IX in the present invention, indicating Form IX is more stable in the ethanol-water system (the volume ratio of ethanol to water is 1:1-1:10) and thus is more suitable for wet granulation.

Those skilled in the art may understand that, under the guidance of this description, some modifications or changes may be made to the present invention. These modifications and changes should be within the scope of the invention as defined in the claims.

What is claimed is:

1. A crystal Form IX of Idelalisib with the structural formula shown below,

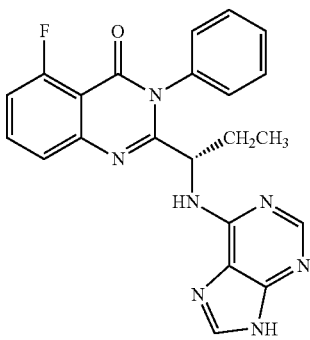

wherein, Form IX is a hydrate with 0.7 molecule of water; and Form IX is characterized by a X-ray powder diffraction pattern measured using Cu-Kα radiation, expressed as 2θ angles, having the following characteristic peaks: 8.8±0.2°, 11.0±0.2°, 13.9±0.2°, 14.9±0.2°, 16.2±0.2° and 20.6±0.2°.

2. The Form IX of Idelalisib according to claim 1, wherein the X-ray powder diffraction pattern of Form IX of Idelalisib, expressed as 2θ angles, has the following characteristic peaks: 8.8±0.2°, 11.0±0.2°, 12.1±0.2°, 13.9±0.2°, 14.9±0.2°, 15.4±0.2°, 16.2±0.2°, 17.1±0.2°, 17.5±0.2°, 20.6±0.2°, 23.2±0.2° and 24.1±0.2°.

3. The Form IX of Idelalisib according to claim 2, wherein the X-ray powder diffraction pattern of Form IX of Idelalisib, expressed as 2θ angles, has the following characteristic peaks and relative intensities:

| diffraction angle 2θ | relative intensity % |
|---|---|
| 8.8 ± 0.2° | 100.0 |
| 11.0 ± 0.2° | 88.1 |
| 12.1 ± 0.2° | 12.1 |
| 13.9 ± 0.2° | 79.4 |
| 14.9 ± 0.2° | 33.3 |
| 15.4 ± 0.2° | 19.9 |
| 16.2 ± 0.2° | 51.2 |
| 17.1 ± 0.2° | 17.3 |
| 17.5 ± 0.2° | 25.6 |
| 20.6 ± 0.2° | 44.7 |
| 20.9 ± 0.2° | 11.2 |
| 21.8 ± 0.2° | 11.6 |
| 23.2 ± 0.2° | 19.8 |
| 23.8 ± 0.2° | 16.0 |
| 24.1 ± 0.2° | 25.5 |
| 24.6 ± 0.2° | 22.5 |
| 27.8 ± 0.2° | 14.2. |

4. The Form IX of Idelalisib according to claim 1, wherein Form IX of Idelalisib is characterized by a FTIR spectrum comprising the following characteristic peaks at the wavenumbers of 1675, 1607, 1472, 1382, 1326, 1301, 1233, 1184, 1100, 1036, 946, 821, 798, 785, 718, 698 and 649 $cm^{-1}$.

5. A method of preparing the Form IX of Idelalisib according to claim 1, comprising:
   suspending Form I of Idelalisib in a solvent system of water and ethanol to form a suspension, stirring or sonicating at a crystallization temperature, and then isolating and drying precipitated solids to obtain Form IX of Idelalisib;
   wherein the volume ratio of ethanol to water in the solvent system is 1:1 to 1:10,
   the amount of Form I of Idelalisib is 1.5-20 times of its solubility in the corresponding solvent system at the crystallization temperature;
   the stirring crystallization temperature is 0° C. to 40° C.;
   the duration of stirring crystallization is 1 to 14 days; and
   the crystallization by sonication is carried out at room temperature, sonicating for 1 to 3 hours at the working power of 20 KHz to 40 KHz.

6. A pharmaceutical composition, comprising a therapeutically effective amount of the Form IX of Idelalisib according to claim 1 and at least one pharmaceutically acceptable excipient.

7. A method of treating the diseases of chronic lymphocytic leukemia, indolent non-Hodgkin's lymphoma, mantle cell lymphoma, diffuse large B cell lymphoma, hodgkin's lymphoma, multiple myeloma, acute myelocytic leukemia, or other hematological malignant tumor, comprising administering to a patient in need thereof an effective amount of the Form IX of Idelalisib according to claim 1.

8. A crystal Form IV of Idelalisib with the structural formula shown below,

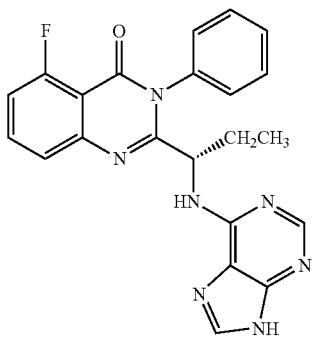

wherein, Form IV is characterized by a X-ray powder diffraction pattern measured using Cu-Kα radiation, expressed as 2θ angles, having the following characteristic peaks: 7.8±0.2°, 9.2±0.2° 14.1±0.2°, 15.7±0.2°, 17.7±0.2°, 18.9±0.2° and 20.7±0.2°.

9. The Form IV of Idelalisib according to claim 8, wherein the X-ray powder diffraction pattern of the Form IV of Idelalisib, expressed as 2θ angles, has the following characteristic peaks: 7.8±0.2°, 9.2±0.2°, 11.5±0.2°, 13.6±0.2°, 14.1±0.2°, 15.7±0.2°, 17.7±0.2°, 18.9±0.2°, 20.2±0.2°, 20.7±0.2°, 21.2±0.2°, 22.2±0.2° and 23.8±0.2°.

10. The Form IV of Idelalisib according to claim 9, wherein the X-ray powder diffraction pattern of the Form IV of Idelalisib, expressed as 2θ angles, has the following characteristic peaks and relative intensities:

| diffraction angle 2θ | relative intensity % |
| --- | --- |
| 7.8 ± 0.2° | 65.7 |
| 9.2 ± 0.2° | 100.0 |
| 11.5 ± 0.2° | 25.9 |
| 13.6 ± 0.2° | 39.2 |
| 14.1 ± 0.2° | 91.4 |
| 15.7 ± 0.2° | 97.9 |
| 17.2 ± 0.2° | 10.5 |
| 17.7 ± 0.2° | 83.5 |
| 18.4 ± 0.2° | 12.8 |
| 18.9 ± 0.2° | 57.3 |
| 20.2 ± 0.2° | 39.3 |
| 20.7 ± 0.2° | 61.5 |
| 21.2 ± 0.2° | 29.6 |
| 21.8 ± 0.2° | 12.3 |
| 22.2 ± 0.2° | 31.2 |
| 22.8 ± 0.2° | 29.4 |
| 23.1 ± 0.2° | 17.6 |
| 23.8 ± 0.2° | 31.6 |
| 25.3 ± 0.2° | 22.2 |
| 25.8 ± 0.2° | 24.1 |
| 26.5 ± 0.2° | 17.0 |
| 27.1 ± 0.2° | 13.8 |
| 27.5 ± 0.2° | 12.5 |
| 27.9 ± 0.2° | 18.1 |
| 29.0 ± 0.2° | 16.3 |
| 29.7 ± 0.2° | 10.7. |

11. The Form IV of Idelalisib according to claim 8, wherein the Form IV of Idelalisib is characterized by a FTIR spectrum comprising the following characteristic peaks at the wavenumbers of 1698, 1628, 1590, 1568, 1475, 1453, 1412, 1329, 1296, 1231, 1152, 1096, 1036, 1025, 937, 901, 818, 801, 779, 755, 721, 694 and 610 cm$^{-1}$.

12. A method of preparing the Form IV of Idelalisib according to claim 8, comprising:
heating Form IX of Idelalisib according to 100~150° C. at a rate of 1 to 15° C./min, keeping isothermal for 1 to 5 minutes until complete form transformation, and then naturally cooling to obtain Form IV of Idelalisib.

13. A pharmaceutical composition, comprising a therapeutically effective amount of the Form IV of Idelalisib according to claim 8 and at least one pharmaceutically acceptable excipient.

14. A method of treating the diseases of chronic lymphocytic leukemia, indolent non-Hodgkin's lymphoma, mantle cell lymphoma, diffuse large B cell lymphoma, hodgkin's lymphoma, multiple myeloma, acute myelocytic leukemia, or other hematological malignant tumor, comprising administering to a patient in need thereof an effective amount of the Form IV of Idelalisib according to claim 8.

15. A crystal Form VI of Idelalisib with the structural formula shown below,

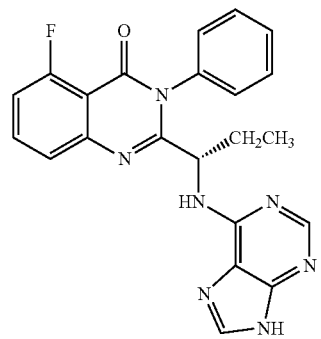

wherein, Form VI is a tetrahydrate, and Form VI is characterized by a X-ray powder diffraction pattern measured using Cu-Kα radiation, expressed as 2θ angles, having the following characteristic peaks: 9.8±0.2°, 11.3±0.2°, 13.3±0.2°, 17.5±0.2°, 19.3±0.2° and 23.2±0.2°.

16. The Form VI of Idelalisib according to claim 15, wherein the X-ray powder diffraction pattern of the Form VI of Idelalisib, expressed as 2θ angles, has the following characteristic peaks: 9.8±0.2°, 11.3±0.2°, 12.5±0.2°, 13.3±0.2°, 17.1±0.2°, 17.5±0.2°, 19.3±0.2°, 22.1±0.2°, 22.7±0.2°, 23.2±0.2°, 23.6±0.2° and 26.4±0.2°.

17. The Form VI of Idelalisib according to claim 16, wherein the X-ray powder diffraction pattern of the Form VI of Idelalisib, expressed as 2θ angles, has the following characteristic peaks and relative intensities:

| diffraction angle 2θ | relative intensity % |
| --- | --- |
| 9.8 ± 0.2° | 100.0 |
| 11.3 ± 0.2° | 28.4 |
| 11.6 ± 0.2° | 13.7 |
| 12.5 ± 0.2° | 25.9 |
| 13.3 ± 0.2° | 47.7 |
| 16.4 ± 0.2° | 12.7 |
| 16.8 ± 0.2° | 14.8 |
| 17.1 ± 0.2° | 24.2 |
| 17.5 ± 0.2° | 35.9 |
| 18.4 ± 0.2° | 30.1 |
| 19.3 ± 0.2° | 46.4 |
| 22.1 ± 0.2° | 25.1 |
| 22.7 ± 0.2° | 23.3 |
| 23.2 ± 0.2° | 46.7 |
| 23.6 ± 0.2° | 30.5 |
| 24.3 ± 0.2° | 11.1 |
| 26.4 ± 0.2° | 24.0 |
| 26.8 ± 0.2° | 12.4 |
| 28.5 ± 0.2° | 14.3 |
| 29.0 ± 0.2° | 19.0. |

18. The Form VI of Idelalisib according to claim 15, wherein the Form VI of Idelalisib is characterized by a FTIR spectrum comprising the following characteristic peaks at the wavenumbers of 3191, 1697, 1632, 1590, 1565, 1475, 1457, 1420, 1394, 1299, 1232, 1185, 1166, 1120, 1039, 1027, 953, 900, 819, 802, 781, 712, 695, 647 and 610 cm$^{-1}$.

19. A method of preparing the Form VI of Idelalisib according to claim 15, comprising:
suspending Form I of Idelalisib in a solvent system to form a suspension, stirring at a crystallization temperature for crystallization, and then isolating and drying precipitated solids to obtain Form VI of Idelalisib;
wherein the solvent system is a solvent mixture of water and isopropanol, or a solvent mixture of water and n-propanol;

the volume ratio of water to isopropanol in the solvent mixture of water and isopropanol is 0.5:1 to 50:1, the volume ratio of water to n-propanol in the solvent mixture of water and n-propanol is 0.5:1 to 50:1; and the amount of Form I of Idelalisib is 1.5 to 20 times of its solubility in the corresponding solvent system at the crystallization temperature; the crystallization temperature is 0° C. to 40° C.

20. A pharmaceutical composition, comprising a therapeutically effective amount of the Form VI of Idelalisib according to claim 15 and at least one pharmaceutically acceptable excipient.

21. A method of treating the diseases of chronic lymphocytic leukemia, indolent non-Hodgkin's lymphoma, mantle cell lymphoma, diffuse large B cell lymphoma, hodgkin's lymphoma, multiple myeloma, acute myelocytic leukemia, or other hematological malignant tumor, comprising administering to a patient in need thereof an effective amount of the Form VI of Idelalisib according to claim 15.

22. A crystal Form III of Idelalisib with the structural formula shown below,

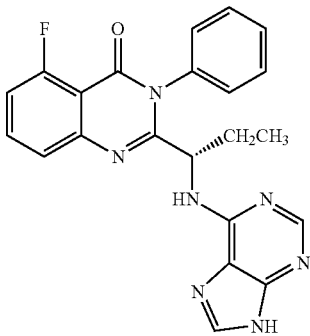

wherein, Form III is characterized by a X-ray powder diffraction pattern measured using Cu-Kα radiation, expressed as 2θ angles, having the following characteristic peaks: 9.3±0.2°, 12.8±0.2°, 14.2±0.2°, 15.9±0.2°, 18.1±0.2° and 18.8±0.2°.

23. The Form III of Idelalisib according to claim 22, wherein the X-ray powder diffraction pattern of the Form III of Idelalisib, expressed as 2θ angles, has the following characteristic peaks: 12.3±0.2°, 12.8±0.2°, 14.2±0.2°, 15.9±0.2°, 16.3±0.2°, 17.4±0.2°, 17.9±0.2°, 18.1±0.2°, 18.8±0.2°, 19.6±0.2°, 20.6±0.2° and 24.5±0.2°.

24. The Form III of Idelalisib according to claim 23, wherein the X-ray powder diffraction pattern of Form III of Idelalisib, expressed as 2θ angles, has the following characteristic peaks and relative intensities:

| diffraction angle 2θ | relative intensity % |
|---|---|
| 11.9 ± 0.2° | 11.1 |
| 12.3 ± 0.2° | 59.3 |
| 12.8 ± 0.2° | 16.6 |
| 14.2 ± 0.2° | 16.9 |
| 15.9 ± 0.2° | 18.2 |
| 16.3 ± 0.2° | 14.3 |
| 17.4 ± 0.2° | 18.4 |
| 17.9 ± 0.2° | 18.1 |
| 18.1 ± 0.2° | 27.0 |
| 18.8 ± 0.2° | 100.0 |
| 19.6 ± 0.2° | 10.6 |
| 20.6 ± 0.2° | 13.5 |
| 21.4 ± 0.2° | 11.2 |
| 24.2 ± 0.2° | 14.8 |
| 24.5 ± 0.2° | 19.1. |

25. The Form III of Idelalisib according to claim 22, wherein the Form III of Idelalisib is characterized by a FTIR spectrum comprising the following characteristic peaks at the wavenumbers of 1689, 1623, 1589, 1569, 1473, 1454, 1384, 1328, 1300, 1251, 1231, 1159, 1098, 1067, 1036, 914, 820, 780, 766, 727, 696, 668 and 618 cm$^{-1}$.

26. A method of preparing the Form III of Idelalisib according to claim 22, which is selected from any one of the following methods, comprising:
1) suspending Form I of Idelalisib in a solvent system to form a suspension, stirring the suspension at a crystallization temperature for crystallization, and then isolating and drying precipitated solids to obtain Form III of Idelalisib;
  wherein the solvent system is selected from the group consisting of acetonitrile, nitromethane, and a solvent mixture of water and acetone at a volume ratio 2:1 to 1:2; and
  the amount of Form I of Idelalisib is 1.5 to 20 times of its solubility in the corresponding solvent system at the crystallization temperature; the crystallization temperature is 0 to 40° C.; the duration of crystallization is 1 to 14 days;
2) slurrying Form IV of Idelalisib in nitromethane for crystallization, and then isolating and drying precipitated solids to obtain Form III of Idelalisib;
  wherein the amount of Form IV of Idelalisib is 1.5 to 20 times of its solubility in nitromethane; and
  the slurry crystallization temperature is 0 to 40° C., the duration of slurry crystallization is 3 to 10 days.

27. A pharmaceutical composition, comprising a therapeutically effective amount of the Form III of Idelalisib according to claim 22 and at least one pharmaceutically acceptable excipient.

28. A method of treating the diseases of chronic lymphocytic leukemia, indolent non-Hodgkin's lymphoma, mantle cell lymphoma, diffuse large B cell lymphoma, hodgkin's lymphoma, multiple myeloma, acute myelocytic leukemia, or other hematological malignant tumor, comprising administering to a patient in need thereof an effective amount of the Form III of Idelalisib according to claim 22.

* * * * *